United States Patent [19]

Vetter et al.

[11] Patent Number: 5,352,603
[45] Date of Patent: Oct. 4, 1994

[54] HIGHLY ALKALINE PROTEASES

[75] Inventors: Roman Vetter, Burgdorf; Detlef Wilke, Wennigsen, both of Fed. Rep. of Germany; Antoine Amory, Rixensart; André Clippe, Brussels, both of Belgium; Dietmar Schomburg; Wolfgang Aehle, both of Brunswick, Fed. Rep. of Germany

[73] Assignees: Kali-Chemie AG, Hanover; Gesellschaft fuer Biotechnologische Forschung mbH, Brunswick, both of Fed. Rep. of Germany

[21] Appl. No.: 661,378

[22] Filed: Feb. 28, 1991

Related U.S. Application Data

[63] Continuation-in-part of Ser. No. 573,802, Aug. 29, 1990, abandoned.

[30] Foreign Application Priority Data

Aug. 31, 1989 [DE] Fed. Rep. of Germany ....... 3928804
Jul. 24, 1990 [DE] Fed. Rep. of Germany ....... 4023458

[51] Int. Cl.$^5$ ................. C12N 9/54; C12N 9/52; C11D 7/42; C11D 3/386
[52] U.S. Cl. ................. 435/221; 435/212; 435/219; 252/174.12
[58] Field of Search ............. 435/172.3, 212, 219, 435/221; 252/174.12

[56] References Cited

U.S. PATENT DOCUMENTS

| | | | |
|---|---|---|---|
| Re. 30,602 | 5/1981 | Tenijenhuis | 435/221 |
| 4,760,025 | 7/1988 | Estell et al. | 435/222 |
| 4,990,452 | 2/1991 | Bryan et al. | 435/222 |
| 5,116,741 | 5/1992 | Bryan et al. | 435/88 |
| 5,155,033 | 10/1992 | Estell et al. | 435/221 |
| 5,182,204 | 1/1993 | Estell et al. | 435/221 |
| 5,185,258 | 2/1993 | Caldwell et al. | 435/221 |
| 5,244,791 | 9/1993 | Estell | 435/219 |
| 5,246,849 | 9/1993 | Bryan et al. | 435/219 |

FOREIGN PATENT DOCUMENTS

| | | |
|---|---|---|
| 130756 | 12/1984 | European Pat. Off. . |
| 328229 | 8/1989 | European Pat. Off. . |
| 0405901A1 | 1/1991 | European Pat. Off. . |
| 0405902A1 | 1/1991 | European Pat. Off. . |
| WO91/00345 | 1/1991 | PCT Int'l Appl. . |
| 8906279 | 7/1989 | World Int. Prop. O. . |

OTHER PUBLICATIONS

Meloun et la, *FEBS Letters* 183:195–199, Apr. 1985.
Reeck et al., "Homology' in Proteins and Nucleic Acids ...", *Cell* 50: 667, Aug. 28, 1987.
Dayhoff, *Atlas of Protein Sequence and Structure*, 1972 p. 96.
Creighton, *Proteins*, 1983, p. 7.
Shulz and Schirmer, *Principles of Protein Structure*, 1979, pp. 14–16.
Wells et al., "Subtilisin–an enzyme designed to be engineered", *Trends in Biochemical Sciences*, 13:291–97 (1988).

*Primary Examiner*—Robert A. Wax
*Assistant Examiner*—Stephen Walsh
*Attorney, Agent, or Firm*—Evenson, McKeown, Edwards & Lenahan

[57] ABSTRACT

Novel, optimized highly alkaline proteases which are suitable for use in detergent formulations are prepared by employing microorganisms transformed by mutated DNA sequences. The mutated sequences are obtained starting from DNA sequences which code for highly alkaline protease usually produced by Bacillus species by altering these DNA sequences in defined positions by directed mutagenesis (point mutation) in such a way that the codon in which the point mutation is located now codes for an amino acid which is more strongly basic than the original amino acid. The result is highly alkaline proteases in which original amino acids have been replaced by more strongly basic amino acids, preferably by the amino acids lysine or arginine. Synthetic oligonucleotides, DNA sequences, vectors and transformed microorganisms which are used for generating and obtaining the optimized highly alkaline protease are also described.

16 Claims, 20 Drawing Sheets

```
CTCGGGAAGCCGATTTGCTACTGCATGTCGTCGATTATTCAAAATGAAACGCCATCGGGAAATGGGCAAAGACGACAAATGAAACACTCCAGGCAATGGAAAT
         10        20        30        40        50        60        70        80        90       100
AVAI(1)                                                                                          CLAI(1)

CGATCGCCCGATGATTTATGTTTACAACAAAATGGATCAAGTGAAAGACGCGTTTCCTCAAGCGCATGGCACGAGCTGTTTATATCAGCTAAGGCTAAAC
        110       120       130       140       150       160       170       180       190       200
PVLI(1)                                       MLUI(1)                                       DDEI(1)

AAGGGCTTGATTTATTAGCACAGAAAATAGCAAGCTATGTTTTTCAAGATTTTGAAAAACATCTCGTTCATCATTCCTTATCGTGACGGGGAGGCGGCTGC
        210       220       230       240       250       260       270       280       290       300

TTATTTAAACAACCATGCCCATGTCACACACAGCGTGCTGAGGAGACGGCTGGCATATCGTTGCCGATTTGCATGAACGAGACTTAAAACGGGTTGAAA
        310       320       330       340       350       360       370       380       390       400
                                DDEI(2)

GCTACTGTGTTCAAAAGAACGATAATGAAAAAGCCATTGAATGCTTCTTTGTTCAAATGGCTTTTTGGGCGACTATGGTAGACAGATGAACACTTGTTT
        410       420       430       440       450       460       470       480       490       500
                                                                                ACCI(1)

CGCTGTTTACGACAAAGATCATCTTGCCTGTTACGCGTTTTTTAAATCCGTTTCAATTGTCGCCGAGTCGATCCAGTCGCTGTAAGTGAG
        510       520       530       540       550       560       570       580       590       600
                MLUI(2)                                                              ALWNI(1)
```

FIG. 1a

```
AATATGTTTAGAAAAGCCGCGTATTTAAGGCGCAGTCTTTTCGTTCTGTACTGGCTGGTTTGTGGACAGTTTCCATACCCATCAACCTCCTTTATTTGTA
   610       620       630       640       650       660       670       680       690       700

GCTTTCCCCACTTGAAACCGTTTAATCAAAAACAAGTGAGAAGATTCAGTTAACTTAACGTTAATATTTGTTCCCAATAGGCAAATCTTTCTAACTTT
   710       720       730       740       750       760       770       780       790       800
                                               HPAI(1)      SSPI(1)
                                               HINCII(1)

MetLysLysProLeuGlyLysIleValAlaSerThrAlaLeuLeu
GATACGTTTAAAACTACCAGCTTGGACAAGTTGGTATAAAAATGAGGAGGAACCGAATGAAGAAACCGTTGGGGAAAATTGTCGCAAGCACCGCACTACT
   810       820       830       840       850       860       870       880       890       900
                                   >><<

IleSerValAlaPheSerSerSerIleAlaSerAlaAlaGluGluLysGlyTyrLeuIleGlyPheAsnGluGlnGluAlaValSerGluPhe
CATTCTGTTGCTTTTAGTTCATCGATCGCATCGGCTGCTGAAGAAGAAAGAAAATATTTAATTGGCTTTAATGAGCAGGAAGCTGTCAGTGAGTTT
   910       920       930       940       950       960       970       980       990      1000
          CLAI(2)                                          SSPI(2)
          PVUI(2)

ValGluGlnValGluAlaAsnAspGluAlaValValAlaIleLeuLeuSerGluGluValGluIleGluPheGluThrIleProValLeu
GTAGAACAAGTAGAGGCAAATGACGAGGCTGCCATTCTCTCTGAGGAAGAAGTGGAAATTGAATTCGAAACGATTCCTGTTTAT
  1010      1020      1030      1040      1050      1060      1070      1080      1090      1100
  TTH111(1)      DDEI(3)                                            XMNI(1)          XMNI(2)
```

FIG.1b

```
                                                                          Protease
                                                                             1
SerValGluLeuSerProGluAspValAspAlaLeuGluLeuAspProAlaIleSerTyrIleGluGluAspAlaGluValThrThrMetAlaGlnSerVal
CCGTTGAGTTAAGCCCAGAAGATGTGGACGCGCTTGAACTCGATCCAGCGATTTCTTATATTGAAGAGGATGCAGAAGTAACGACAATGGCGCAATCAGT
1110       1120       1130       1140       1150       1160       1170       1180       1190       1200
                                                                Lys                            Arg
 5                  10                 15                 20                 25                 30                 35
ProTrpGlyIleSerArgValGlnAlaProAlaAlaHisAsnArgGlyLeuThrGlySerGlyValLysValAlaValLeuAspThrGlyIleSerThr
GCCATGGGGAATTAGCCGTGTGCAAGCTCCTGCCCATGCCCCATAACCGTGGATTGACAGGTTCTGGTGTAAAAGTTGCTGTCCTCGATACAGGTATTTCCACT
1210       1220       1230       1240       1250       1260       1270       1280       1290       1300

STYI(1)                           PVUII(1)          ALWNI(2)
NCOI(1)                           BSTXI(1)

40                 45                 50                 55                 60                 65                 70
HisProAspLeuAsnIleArgGlyGlyAlaSerPheValProGlyGluProSerThrGlnAspGlyAsnGlyHisGlyThrHisValAlaGlyThrIle
CATCCAGATTTAAATATTCGTGGTGGCGCTAGCTTTGTACCAGGGGAACCATCCACTCAAGATGGGAATGGGCACGCATGGCCGGGACGATTG
1310       1320       1330       1340       1350       1360       1370       1380       1390       1400

SSPI(3)        HAEIII(1)                                                                           PALI(1)
                                                                                                   HAEIII(1)
                                                                                                   HPAII(1)
                                                                                                   MSPI(1)

75                 80                 85                 90                 95                 100
AlaAlaLeuAsnAsnSerIleGlyValLeuGlyValAlaProSerAlaGluLeuTyrAlaValLysValLeuGlyAlaSerGlySerGlyValSerSer
CTGCTTTAAACAATTCGATTGGCGTTCTTGGCGTAGCGCCGAGCGCGGAACTATACGCTGTTAAAGTATTAGGGGCGAGCGGTTCAGGTTCGGTCAGCTC
1410       1420       1430       1440       1450       1460       1470       1480       1490       1500

HAEIII(2)
```

FIG.1c

```
            Lys               Arg                                                       Lys
105         110               115            120            125            130         135
IleAlaGlnGlyLeuGluTrpAlaGlyAsnAsnGlyMetHisValAlaAsnLeuSerLeuSerProSerAlaThrLeuGluGlnAlaVal
GATTGCCCAAGGATTGGGAATGGGCAGGGAACAATGGCATGGCACGTTGCTAATTTGAGTTTAGGAAGCCCTTCGCCACACTTGAGCAAGCTGTT
1510        1520              1530           1540           1550           1560           1570           1580           1590           1600

STYI(2)                            SPHI(1)                                        XMNI(3)

Arg
            140        145           150              155           160              165            170
AsnSerAlaThrSerArgGlyValLeuValValAlaAlaSerGlyAsnSerGlyAlaGlySerIleSerTyrProAlaArgTyrAlaAsnAlaMetAla
AATAGCGCGACTTCTAGAGGCGTTCTTGTTGTAGCGGCATCTGGGAATTCAGGTGCAGGCTCAATCAGCTATCCGGCCCGTTATGCGAACGCAATGGCAG
1610         1620           1630           1640           1650           1660           1670           1680           1690           1700

XBAI(1)                             ECORI(1)                             HPAII(2)
  MAEI(1)                                                                  MSPI(2)
                                                                           SAU96I(1)
                                                                           PALI(2)
                                                                           HAEIII(2)

175           180          185             190           195            200
ValGlyAlaThrTyrGlnAsnAsnAsnArgAlaSerPheSerGlnTyrGlyAlaGlyLeuAspIleValAlaProGlyValAlaAsnValGlnSerThrTyrPro
TCGGAGCTACTGACCAACAAAACAACCGCGCCAGCTTTTCACAGTATGGCGCAGGGCTTGACATTGTCGCACCAGGTGTAAACGTGCAGAGCACATACCC
1710         1720           1730           1740           1750           1760           1770           1780           1790           1800

TTH111(2)

205           210           215          220             225           230            235
GlySerThrTyrAlaSerLeuAsnGlyThrSerMetAlaThrProHisValAlaAlaAlaAlaLeuValLysGlnLysAsnProSerTrpSerAsn
AGGTTCAACGTATGCCAGCTAAACGGTACACGGATGGCTACCTCCTCATGTTGCAGGTGCAGCAGCCCTTGTTAAACAAAGAACCCATCTTGGTCCAAT
1810         1820           1830           1840           1850           1860           1870           1880           1890           1900

CLAI(3)                                                                                SAU96I(2)
                                                                                           AVAII(1)
```

FIG. 1d

```
                    240                 245                 250                 255                 260                 265
          ValGlnIleArgAsnHisLeuLysAsnThrAlaThrSerLeuGlySerThrThrAsnLeuTyrGlySerGlyLeuValAsnAlaAlaGluAlaAlaThrArg>>>
          GTACAAATCCGCAATCATCTAAAGAATACGGCAACGAGCTTAGGAAGCACGAACTTGTATGGAAGCGGACTTGTCAATGCAGAAGCGGCAACACGCTAAT
            1910                1920                1930                1940                1950                1960                1970                1980                1990                2000

CAATAAAAAAAAGCCTGTGCGGTTAAAGGGCACAGCGTTTTTTGTGTATGAATCGAAAAAGAGAACAGATCGCAGGTCTCAAAAATCGAGCGTAAAGGGC
            2010                2020                2030                2040                2050                2060                2070                2080                2090                2100

TGTTTAAAGCTCTTTACGCTCGCAGGTCTTATCGCTATACAATGGAAAATTCACGTCTCTTTGACTTTCATGGCATATTTATTTAAGTATTCGTTTGCTTT
            2110                2120                2130                2140                2150                2160                2170                2180                2190                2200

TTCGTACTCTCCGTTTTTCTGGTACCATTGCGCCAGCTCAATTGCATAGTGGACTGGTTCTTCTTTATTATCAAGCTT
            2210                2220                2230                2240                2250                2260                2270                2280

ASP718(1)                                                                HINDIII(1)
          KPNI(1)
```

FIG. 1e

I. Asn18 ---> Lys: (N18K)

```
                                        14  15  16  17  18  19  20
                                       Pro Ala Ala His Asn Arg Gly
Sequence of the Starting Protease     :CCA GCT GCC CAT AAC CGT GGA
                                           Pvu2
Oligonucleotide                       :CCA GCa GCC CAT AAg CGT GCA
New Amino Acid                        :                   Lys
```

II. Lys27 --->Arg: (K27R)

```
                                        24  25  26  27  28  29  30  31  32  33
                                       Ser Gly Val Lys Val Ala Val Leu Asp Thr
Sequence of the Starting Protease     :TCT GGT GTA AAA GTT GCT GTC CTC GAT ACA
                                                                   ScaI
Oligonucleotide                       :TCT GGT GTA cgt GTT GCa GTa CTC GAT ACA
New Amino Acid                        :            Arg
```

III. Asn42 --->Arg: (N42R)

```
                                        39  40  41  42  43  44  45
                                       Pro Asp Leu Asn Ile Arg Gly
Sequence of the Starting Protease     :CCA GAC TTA AAT ATT CGT GGT
                                                   SnaBl
Oligonucleotide                       :CCA GAC TTA cgt ATT CGT GGT
New Amino Acid                        :            Arg
```

IV. Gln57 --->Arg: (Q57R)

```
                                        53  54  55  56  57  58  59  60  61
                                       Glu Pro Ser Thr Gln Asp Gly Asn Gly
Sequence of the Starting Protease     :GAA CCA TCC ACT CAA GAT GGG AAT GGG
                                                       MluI
Oligonucleotide                       :GAA CCA TCC ACg CGt GAT GGG AAT GGG
New Amino Acid                        :                Arg
```

V. Ala96 --->Arg: (A96R)

```
                                        91  92  93  94  95  96  97  98  99
                                       Val Lys Val Leu Gly Ala Ser Gly Ser
Sequence of the Starting Protease     :GTT AAA GTA TTA GGG GCG AGC GGT TCA
                                                       ScaI
Oligonucleotide                       :GTT AAA GTA cTt GGG cgt AGC GGT TCA
New Amino Acid                        :                    Arg
```

FIG. 4a

VI. Gln107--->Arg: (Q107R)

```
                                   104 105 106 107 108 109 110
                                   Ser Ile Ala Gln Gly Leu Glu
Sequence of the Starting Protease :TCG ATT GCC CAA GGA TTG GAA
                                           BssH2
Oligonucleotide                   :TCG ATT GCg Cgc GGA TTG GAA
New Amino Acid                    :               Arg
```

VII. Asn114--->Arg: (N114R)

```
                                   111 112 113 114 115 116 117 118
                                   Trp Ala Gly Asn Asn Gly Met His
Sequence of the Starting Protease :TGG GCA GGG AAC AAT GGC ATG CAC
                                                           Sph1
Oligonucleotide                   :TGG GCA GGG cgt AAT GGt ATG CAC
New Amino Acid                    :           Arg
```

VIII. Asn115--->Arg: (N115R)

```
                                   111 112 113 114 115 116 117 118 119
                                   Trp Ala Gly Asn Asn Gly Met His Val
Sequence of the Starting Protease :TGG GCA GGG AAC AAT GGC ATG CAC GTT
                                           BstE2
Oligonucleotide                   :TGG GCA GGt AAC cgT GGC ATG CAC GTT
New Amino Acid                    :               Arg
```

IX. Gln135--->Arg: (Q135R)

```
                                   132 133 134 135 136 137 138 139 140
                                   Thr Leu Glu Gln Ala Val Asn Ser Ala
Sequence of the Starting Protease :ACA CTT GAG CAA GCT GTT AAT AGC GCG
                                                       Hinc2
Oligonucleotide                   :ACA CTT GAG Cgt GCT GTT AAc AGC GCG
New Amino Acid                    :           Arg
```

X. Gln138--->Arg: (N138R)

```
                                   134 135 136 137 138 139 140 141 142
                                   Glu Gln Ala Val Asn Ser Ala Thr Ser
Sequence of the Starting Protease :GAG CAA GCT GTT AAT AGC GCG ACT TCT
                                                   SnaB1
Oligonucleotide                   :GAG CAA GCT GTa cgT AGC GCG ACT TCT
New Amino Acid                    :                Arg
```

FIG. 4b

XI. Ala166--->Arg: (A166R)

|  |  | 162 | 163 | 164 | 165 | 166 | 167 | 168 | 169 | 170 |
|---|---|---|---|---|---|---|---|---|---|---|
|  |  | Pro | Ala | Arg | Tyr | Ala | Asn | Ala | Met | Ala |
| Sequence of the Starting Protease | :CCG | GCC | CGT | TAT | GCG | AAC | GCA | ATG | GCA |
|  |  |  | BssH2 |  |  |  |  | NcoI |  |  |
| Oligonucleotide | :CCG | GCg | CGc | TAT | cgt | AAC | GCc | ATG | GCA |
| New Amino Acid | : |  |  |  | Arg |  |  |  |  |

XII. Val 238--->Arg: (V238R)

|  |  | 234 | 235 | 236 | 237 | 238 | 239 | 240 | 241 |
|---|---|---|---|---|---|---|---|---|---|
|  |  | Ser | Trp | Ser | Asn | Val | Gln | Ile | Arg |
| Sequence of the Starting Protease | :TCT | TGG | TCC | AAT | GTA | CAA | ATC | CGC |
|  |  |  |  |  | HinfI |  |  |  |  |
| Oligonucleotide | : CT | TGG | TCg | ATT | cgt | CAA | ATC | CG |
| New Amino Acid | : |  |  |  | Arg |  |  |  |

XIII. Asn255-->Arg: (N255R)

|  |  | 251 | 252 | 253 | 254 | 255 | 256 | 257 | 258 | 259 |
|---|---|---|---|---|---|---|---|---|---|---|
|  |  | Leu | Gly | Ser | Thr | Asn | Leu | Tyr | Gly | Ser |
| Sequence of the Starting Protease | :TTA | GGA | AGC | ACG | AAC | TTG | TAT | GGA | AGC |
|  |  |  |  |  | MluI |  |  |  |  |  |
| Oligonucleotide | :TTA | GGA | AGC | ACG | cgt | TTG | TAT | GGA | AGC |
| New Amino Acid | : |  |  |  | Arg |  |  |  |  |

XIV. Ser 259 -->Lys: (S259K)

|  |  | 255 | 256 | 257 | 258 | 259 | 260 | 261 | 262 | 263 | 264 |
|---|---|---|---|---|---|---|---|---|---|---|---|
|  |  | Asn | Leu | Tyr | Gly | Ser | Gly | Leu | Val | Asn | Ala |
| Sequence of the Starting Protease | :AAC | TTG | TAT | GGA | AGC | GGA | CTT | GTC | AAT | GCA |
|  |  |  |  |  |  | StuI |  |  |  |  |  |
| Oligonucleotide | : C | TTG | TAT | GGA | aaa | GGc | CTT | GTC | AAT | GC |
| New Amino Acid | : |  |  |  | Lys |  |  |  |  |  |

XV. Ala266-->Arg: (A266R)

|  |  | 259 | 260 | 261 | 262 | 263 | 264 | 265 | 266 | 267 | 268 | 269 |
|---|---|---|---|---|---|---|---|---|---|---|---|---|
|  |  | Ser | Gly | Leu | Val | Asn | Ala | Glu | Ala | Ala | Thr | Arg |
| Sequence of the Starting Protease | : AGC | GGA | CTT | GTC | AAT | GCA | GAA | GCG | GCA | ACA | CGC |
|  |  |  |  |  | HpaI |  |  |  |  |  |  |
| Oligonucleotide | : GC | GGA | CTT | GTt | AAc | GCA | GAA | cgt | GCA | ACA | CGC |
| New Amino Acid | : |  |  |  |  |  |  | Arg |  |  |  |

FIG. 4c

|  | NcoI/StyI |
|---|---|
|  | Pro Trp |
| Original repU-Sequence: | AAA GTG AGA CCA TGG AGA GAA AA |
| Synthetic Oligonucleotide: | AAA GTG AGA CCg TGG AGA GAA AA |

HIGHLY ALKALINE PROTEASES

This application is a continuation-in-part of copending application Ser. No. 07/573,802 filed Aug. 29, 1990, now abandoned.

BACKGROUND OF THE INVENTION

The present invention relates to highly alkaline proteases optimized by directed mutagenesis of DNA sequences coding for highly alkaline proteases, to DNA sequences (genes) which code for these proteases, to vectors which contain these DNA sequences, and to microorganisms transformed with these vectors, to a process for preparing optimized highly alkaline proteases, and to detergents containing the optimized proteases.

Highly alkaline proteases are valuable industrial products with advantageous applications, especially in the detergent industry, because they remove protein-containing impurities. In order to be effective, these proteases must not only have proteolytic activity under the laundering conditions (pH, temperature) but additionally be compatible with other detergent ingredients, that is to say in combination with other enzymes, surfactants, builders, bleaching agents, bleaching agent activators, and other additives and auxiliaries, that is to say display an adequate stability with respect to the latter and an adequate activity in the presence of these substances.

Highly alkaline proteases are special enzymes which are obtained by cultivation of microorganisms, especially by cultivation of Bacillus species which, like, for example, *Bacillus alcalophilus*, produce the desired highly alkaline protease and excrete it into the culture medium, from which the protease can be isolated. These highly alkaline proteases differ from usual alkaline proteases as can be obtained by cultivation of Bacillus species such as, in particular, for example *B. subtilis, B. amyloliquefaciens* and *B. licheniformis*.

Although many attempts have been made in the prior art to obtain novel highly alkaline proteases with desired properties, and a number of natural and artificially modified (by genetic engineering) alkaline and highly alkaline proteases have been disclosed, there is still a need for novel, optimized highly alkaline proteases, especially highly alkaline proteases optimized with regard to washing properties.

SUMMARY OF THE INVENTION

Hence the object was to prepare novel, valuable highly alkaline proteases with optimized properties, to generate the DNA sequences (genes) required for this by directed mutagenesis, and to make available the required vectors and transformed microorganisms.

The object is achieved by the highly alkaline proteases according to the invention, by the relevant DNA sequences (genes), vectors and transformed microorganisms, and by the process according to the invention.

DETAILED DESCRIPTION OF THE PREFERRED EMBODIMENTS

The invention relates to highly alkaline proteases which are distinguished in that they have an amino-acid sequence which has at least 80% homology with the amino-acid sequence indicated in FIG. 1 (SEQ. ID. NO. 2) and differs from the latter in at least one of the positions 18, 27, 42, 49, 57, 96, 107, 114, 115, 135, 138, 166, 176, 179, 188, 189, 198, 238, 255, 259, 266 in FIG. 1, (SEQ. ID. NO. 2) preferably 18, 27, 42, 57, 96, 107, 114, 115, 135, 138, 166, 238, 255, 259, 266, or in one of the positions homologous thereto, in that the amino acid located in the relevant position has been replaced by a more strongly basic amino acid. These highly alkaline proteases have molecular weights of 26000 to 28000 g/mole measured by SDS polyacrylamide gel electrophoresis comparing with reference proteins of known molecular weight. They are additionally distinguished by a pH optimum in the range from 10 to 12.5, the pH optimum being defined as that pH range in which the proteases display maximum proteolytic activity. The pH stability of the proteases according to the invention is essentially unchanged from that of the initial protease, that is to say is equally good. The proteases in a preferred embodiment of the invention have amino-acid sequences with a homology of above 90% but especially of above 95%, with the amino-acid sequence of FIG. 1 (SEQ. ID. NO. 2) and have at least one amino acid in one of the indicated positions replaced by a more strongly basic amino acid.

Homology with the amino-acid sequence indicated in FIG. 1 (SEQ. ID. NO. 2) is defined in this connection as a very close structural relationship of the relevant amino-acid sequences with the amino-acid sequence indicated in FIG. 1 (SEQ. ID. NO. 2). To determine the homology, in each case the structurally mutually corresponding sections of the amino-acid sequence of FIG. 1 (SEQ. ID. NO. 2) and of the amino-acid sequence to be compared therewith are superimposed in such a way that the structural correspondence between the amino-acid sequences is a maximum, account being taken of differences caused by deletion or insertion of individual amino acids, and being compensated by appropriate shifts in sections of the sequences. The homology in % results from the number of amino acids which now correspond to one another in the sequences ("homologous positions") relative to the total number of amino acids contained in the sequence of FIG. 1 (SEQ. ID. NO. 2). Differences in the sequences may be caused by variation, insertion or deletion of amino acids.

Accordingly, it is apparent that the amino-acid positions identified with reference to FIG. 1 (SEQ. ID. NO. 2) in the highly alkaline proteases according to the invention, which have been obtained from proteases at least 80% homologous with FIG. 1, relate to the positions homologous thereto of the proteases according to the invention. Deletions or insertions in the proteases homologous with FIG. 1 (SEQ. ID. NO. 2) may lead to a relative shift in the amino-acid positions so that the numerical identifications of the amino-acid positions corresponding to one another are not necessarily identical in homologous fragments of amino-acid sequences which are homologous with one another.

The number of mutations introduced into a protease is subject to no restrictions. It is possible, in particular, in the proteases optimized according to the invention for amino acids in one or more, preferably in from 1 to 3, particularly preferably in 1 or 2, of the aforementioned positions to be replaced by more strongly basic amino acids. Examples of highly alkaline proteases according to the invention in which amino acids in more than just one position have been replaced by more strongly basic amino acids in the aforementioned positions include, for example, those proteases with at least 80% homology with the amino-acid sequence indicated in FIG. 1, (SEQ. ID. NO. 2) in which the relevant amino acid in two of the said positions, for example in position 27 and 115, 27 and 135, 96 and 266 or in position 107 and 238 has been replaced by one which is more strongly basic.

More strongly basic amino acids suitable for replacing the amino acid originally located in the replacement positions are arginine and lysine. Arginine proves to be especially advantageous. Particularly suitable examples of highly alkaline proteases optimized according to the invention which may be mentioned include, on the one hand, proteases in which the amino acid in position 18 or 259 has been replaced by lysine and, on the other hand, proteases in which the amino acid in position 27, 42, 57, 96, 107, 114, 115, 135, 138, 166, 238, 255 or 266 has been replaced by arginine.

The proteases according to the invention are obtained by cultivating microorganisms which have been transformed with an expression vector which contains the structural gene coding for the relevant protease; the expression vectors for this have been obtained by processes described hereinafter. The development of these processes also embraces the sequencing of the protease of FIG. 1 (SEQ. ID. NO. 2).

Hence the invention also embraces those transformed microorganisms, expression vectors and other vectors, as well as protease structural genes (that is to say DNA sequences coding for the protease) which are of particular importance for processes for the sequencing of the protease of FIG. 1 (SEQ. ID. NO. 2) or for the construction and obtaining of the highly alkaline proteases according to the invention.

The DNA sequences according to the invention are distinguished in that they code for a highly alkaline protease which has an amino-acid sequence which has at least 80% homology with the amino-acid sequence indicated in FIG. 1 (SEQ. ID. NO. 2) and differs from the latter in at least one of the positions 18, 27, 42, 49, 57, 96, 107, 114, 115, 135, 138, 166, 176, 179, 188, 189, 198, 238, 255, 259, 266 in FIG. 1, preferably 18, 27, 42, 57, 96, 107, 114, 115, 135, 138, 166, 238, 255, 259, 266, or in one of the positions homologous thereto, in that the amino acid located in the relevant position has been replaced by a more strongly basic amino acid. Preferred DNA sequences according to the invention are those which code for highly alkaline proteases having amino-acid sequences which have a homology of more than 90%, but especially of more than 95%, with the amino-acid sequence of FIG. 1 (SEQ. ID. NO. 2) and in which at least one amino acid in one of the indicated positions has been replaced by a more strongly basic amino acid. The DNA sequences according to the invention may code, in particular, for the aforementioned amino-acid sequences in which amino acids in 1 to 3, preferably in 1 or 2, of the aforementioned positions have been replaced by more strongly basic amino acids. Examples of proteases which are encoded by these DNA sequences according to the invention and in which more than one, for example two, amino acids have been replaced have already been indicated hereinbefore for the appropriate highly alkaline proteases according to the invention.

In a particular embodiment of the DNA sequences according to the invention, the latter are distinguished in that they code for highly alkaline proteases in which the relevant amino acid has been replaced by the more strongly basic amino acid lysine or arginine, but especially by arginine. Particularly advantageous examples of DNA sequences according to the invention which may be mentioned include, on the one hand, DNA sequences which code for highly alkaline proteases in which the amino acid in position 18 or 259 has been replaced by lysine and, on the other hand, DNA sequences which code for highly alkaline proteases in which the amino acid in position 27, 42, 57, 96, 107, 114, 115, 135, 138, 166, 238, 255 or 266 has been replaced by arginine.

The DNA sequences described above are contained, for example, in the vectors according to the invention, which are suitable for the transformation of microorganisms. These vectors can be, in particular, expression vectors which are suitable for the transformation of those microorganisms which can be employed for preparing and obtaining highly alkaline proteases; it is also desirable, for production of the proteases according to the invention on an industrial scale, to integrate the DNA sequences according to the invention, which are described above, in the genome of the microorganism used for the production.

The preferred vectors are plasmids. One group of plasmids used here contains DNA sequences from $E.$ $coli$ which code for $\beta$-lactamase (marker; for example ampicillin resistance) and for the $E. coli$ origin of replication (contains the genetic information required for the plasmid to be able to replicate in $E. coli$), DNA sequences which code for antibiotic resistance (marker; for example kanamycin or neomycin resistance) and for the Bacillus origin of replication (contains the genetic information required for the plasmid to be able to replicate in Bacillus species) in $Bacillus\ subtilis$, the promoter sequence and the prepro sequence for the protease according to the invention, and one of the DNA sequences according to the invention. Plasmids of this type, which can be obtained by the processes described hereinafter, are especially suitable as expression vectors. An example of an expression vector of this type, called pAL1NC, is depicted in the restriction map in FIG. 14.

The vectors according to the invention additionally include vectors which represent precursors of the expression vectors according to the invention which are described above. In one variant, the vector precursors contain all the DNA sequences contained in the expression vector described above, with the exception of the mutated DNA sequence according to the invention which codes for the protease according to the invention. The site of the protease DNA sequence is in this case occupied by a synthetic linker which can be wholly or partly removed by cutting with suitable restriction endonucleases and can be replaced by the protease DNA sequence in a subsequent recombination of the latter with the remaining part of the vector. One example of an expression vector precursor of this type, called pAL1P, is depicted in the restriction map in FIG. 11. The synthetic linker extends in this example from the NcoI (1207) restriction site, via the XbaI (1213) and Asp718 (1219) restriction sites to the HindIII (1225) restriction site. In another variant, the expression vector precursors additionally already contain those parts of the proteases DNA sequences in which no mutations are to be carried out. One vector of this type contains, for example, the N- or C-terminal half of the protease DNA, depending on whether the mutation of the protease DNA takes place by replacement of an amino acid in the C-terminal or the N-terminal half of the protease structural gene. Expression vector precursors of this type are obtained from the aforementioned expression vector precursor of the pAL1P type by replacing a part of the synthetic linker by the N- or C-terminal half of the un-mutated protease structural gene. Examples of these precursors of the complete expression vector, called pAL1N (contains the non-mutated N-terminal half of the protease structural gene, which replaces the NcoI/XbaI fragment of the synthetic linker in the vector pAL1P) and called pAL1C (contains the non-mutated C-terminal half of the protease structural gene, which replaces the XbaI/Asp718 fragment of the synthetic linker in the vector pAL1P), are depicted in the restriction maps in FIG. 12 and FIG. 13, respectively.

The vectors according to the invention additionally include a group of phagemids which is advantageously employed for obtaining mutated N- and C-terminal halves of the protease structural gene. These take the form of, for example, phagemids into which either the N-terminal half, including the promoter belonging to the protease gene and the prepro DNA sequences, or the C-terminal half of the protease structural gene have been incorporated by cutting with suitable restriction endonucleases and subsequent recombination with the appropriate halves of the protease structural gene of the highly alkaline initial protease. Examples of these vectors, called pCLMUTN1 (contains the non-mutated N--terminal half of the structural gene of the highly alkaline initial protease including the relevant prepro and promoter sequences) and called pCLMUTC1 (contains the non-mutated C-terminal half of the structural gene of the highly alkaline initial protease), are depicted in FIG. 5 and FIG. 6.

The vectors according to the invention additionally include a group of plasmids which embraces cloning and expression vectors which, on the one hand, are of importance for the isolation, replication and sequencing of the structural gene of the highly alkaline initial protease and, on the other hand, act as source of the complete protease structural gene or of parts thereof which are required for constructing the vectors described above. These vectors contain DNA sequences which code for antibiotic resistance and for the origin of replication in Bacillus, as well as promoter, prepro and DNA sequences of the highly alkaline initial protease. Examples of such plasmids, called pCLEAN0 and pCLEAN4, are depicted in the restriction maps in FIG. 2 and FIG. 3.

The microorganisms according to the invention are distinguished in that they are transformed with one of the vectors described above according to the invention. Microorganisms which are suitable include all those which are able to express the information of the vectors according to the invention. The microorganisms according to the invention include, on the one hand, transformed microorganisms suitable for producing the protease according to the invention and, on the other hand, also those transformed microorganisms which have been generated for the first time within the scope of the processes, described hereinafter, of sequencing and of directed DNA sequence mutagenesis. The microorganisms which can be used for obtaining the transformed microorganisms for the protease production are those suitable for transformation with an expression vector according to the invention and for production of highly alkaline proteases. These include bacteria which intrinsically already produce protease, preferably Bacillus species, but also microorganisms, such as, for example, bacteria, which are suitable for transformation with an expression vector according to the invention but which do not yet intrinsically produce any protease and acquire this ability only by transformation. Particularly preferable are bacteria which intrinsically already produce alkaline or highly alkaline protease, or the protease-deficient mutants thereof, which are transformed with an expression vector according to the invention; bacteria of this type include, in particular, Bacillus species such as *Bacillus subtilis, Bacillus alcalophilus, Bacillus licheniformis* and *Bacillus amyloliquefaciens*. Examples of other microorganisms according to the invention are bacteria of the species *E. coli* transformed with one of the vectors according to the invention. These microorganisms are particularly suitable for use in processes for constructing vectors according to the invention, in which they are used for the selection and replication of these vectors, and for use in processes for sequencing and for directed mutagenesis, in which they are used for obtaining single-stranded DNA sequences.

The invention also embraces detergent compositions which contain at least one of the highly alkaline proteases according to the invention. For this application the invention provides a group of novel highly alkaline proteases with some improved properties compared with previously known proteases, from which it is possible to select a protease according to the invention which is especially suitable for the particular specific detergent formulation depending on the specifically required properties (washing efficiency, heat resistance, compatibility with other ingredients) of the highly alkaline protease to be employed. The proteases according to the invention can be employed in detergent formulations, especially in powdered detergent formulations, singly or, if desired, also in combination with one another, where appropriate also in combination with prior art detergent proteases or other customary detergent enzymes, such as, for example, amylases, lipases, pectinases, nucleases, oxidoreductases etc. The proteases according to the invention are used in the detergent formulations in amounts customary for detergent enzymes, in particular in amounts of up to 3% by weight (based on the dry matter of the complete composition), preferably in an amount of from 0.2 to 1.5% by weight.

Besides the detergent enzymes already mentioned, the detergents of the invention can contain all customary detergent ingredients, such as surfactants, bleaching agents or builders, as well as other customary additives for formulating detergents in customary amounts. Such additives include, for example, enhancers, enzyme stabilizers, anti-redeposition agents and/or compatibility promoters, complexing and chelating agents, foam regulators and additives such as optical brighteners, opacifying agents, corrosion inhibitors, anti-electrostatics, dyestuffs, bactericides, bleaching agent activators, peracid bleaching agent precursors, etc.

Thus, detergent formulations according to the invention contain, in a typical exemplary composition, based on dry matter a) at least 5% by weight, for example 10 to 50% by weight, of a surfactant or surfactant mixture, b) up to 40% by weight of a builder or of a builder mixture, c) up to 40% by weight of a bleaching agent or bleaching agent mixture, preferably a perborate such as sodium perborate tetrahydrate or sodium perborate monohydrate, d) up to 3% by weight of at least one protease according to the invention, and e) other ingredients such as auxiliaries etc. and 100% by weight.

The detergent formulations of this type can be formulated in a conventional manner. For this purpose, the proteases according to the invention can be mixed, for example in the form of granules, prills or pellets, optionally provided with surface coatings, with the other components of the detergent formulation in a known manner.

The invention furthermore embraces a process for preparing a highly alkaline protease optimized according to the invention, using a microorganism which has been transformed according to the invention and which contains a vector with a DNA sequence which codes for an amino-acid sequence which has at least 80% homology with the amino-acid sequence of the initial protease indicated in FIG. 1 (SEQ. ID. NO. 2) and which differs from the latter in at least one of the positions 18, 27, 42, 49, 57, 96, 107, 114, 115, 135, 138, 166, 176, 179, 188, 189, 198, 238, 255, 259, 266 in FIG. 1 (SEQ. ID. NO. 2), preferably 18, 27, 42, 57, 96, 107, 114, 115, 135, 138, 166, 238, 255, 259, 266, or in one of the positions homologous thereto, in that the amino acid located in the relevant position has been replaced by a more strongly basic amino acid. The microorganism transformed according to the invention is cultivated and an optimized highly alkaline protease with an amino-acid sequence modified compared with the amino-acid sequence of the initial protease in FIG. 1 (SEQ. ID. NO. 2), in at least one of the aforementioned positions by replacement of an amino-acid by a more strongly basic amino-acid, is isolated from the culture medium. The microorganisms preferably employed in this process are those which contain a vector with a DNA sequence which codes for an amino-acid sequence of a highly alkaline protease, where the amino acid sequence of this protease has a homology of more than 90%, especially of more than 95%, with the amino-acid sequence in FIG. 1 (SEQ. ID. NO. 2) and the amino acid in at least one of the indicated positions in the amino-acid sequence has been replaced by a more strongly basic amino acid.

The procedure for generating the microorganisms employed in the aforementioned process can be such that a) initially the DNA sequence coding for the protease (that is to say the structural gene of the protease) is isolated from a suitable bacterium which produces a highly alkaline protease with an amino-acid sequence exhibiting at least 80%, preferably above 90%, and especially above 95%, homology with the amino-acid sequence illustrated in FIG. 1 (SEQ. ID. NO. 2), b) the nucleotide sequence of this DNA sequence is determined, c) the DNA sequence which is now known is subjected to mutations (point mutations) such that the mutated DNA sequence now codes for a highly alkaline protease in which amino acids in the aforementioned positions in the original protease have been replaced by a more strongly basic amino acid, d) subsequently an expression vector is generated using the mutated DNA sequence, and e) the resulting expression vector is transformed into a suitable microorganism which can ultimately be employed for producing the mutated highly alkaline protease.

The process steps for the construction and obtaining of the highly alkaline proteases according to the invention, and the intermediates obtained therein, to some of which the invention likewise relates, in the form of DNA sequences, vectors, especially expression vectors, and transformed microorganisms are described individually in detail hereinafter.

The structural genes which code for amino-acid sequences of highly alkaline proteases with at least 80% homology with the amino-acid sequence indicated in FIG. 1 (SEQ. ID. NO. 2) can be obtained by known general methods. For this purpose, the chromosomal DNA is isolated by known methods, for example from a bacterium ("donor bacterium"), especially from a Bacillus species, which produces the highly alkaline protease, and is partially hydrolyzed with suitable restriction endonucleases. Restriction endonucleases are enzymes which carry out substrate-specific breakdown of double-stranded DNA into fragments by cleaving the phosphate diester linkages between individual nucleotide units in the DNA. All restriction endonucleases are able to recognize particular base sequences of the DNA which indicate specific sites of action (cutting sites) for the activity of the relevant restriction endonucleases. The cutting (restriction) of double-stranded DNA with some restriction endonucleases results in specific, so-called "protruding ends" which, under certain renaturation conditions, can be joined (ligated) together again or to appropriate (complementary) protruding ends of DNA fragments obtained elsewhere (recombination). Cutting with other restriction endonucleases results in DNA double strands with blunt ends. These DNA double strands with blunt ends can be recombined with any desired DNA double strands which likewise have blunt ends.

The resulting restriction fragments of the donor DNA can be fractionated according to size, for example by gel electrophoresis, and the fragments of the desired size can then be recombined with a suitable double-stranded vector DNA.

Vectors are DNA molecules which are suitable as transport molecules (vehicles) for the insertion (transformation) of foreign DNA into host cells, are capable of autonomous replication therein where appropriate, and also have, where appropriate, so-called markers. Markers are DNA fragments which code for particular observable properties (for example antibiotic resistance) and are used for the subsequent selection of the transformed microorganisms (transformants). Frequently used vectors are the so-called plasmids, i.e., extrachromosomal, circular, double-stranded bacterial DNA which can be introduced by suitable methods into other microorganisms and is able to replicate there.

The in vitro recombined DNA (vector+restriction fragments from the donor DNA) can be used to transform bacteria, preferably a Bacillus species, and the transformants can be selected for the known marker property (for example neomycin resistance). This results in clones, that is to say genetically identical transformants. Those among these transformants which show increased protease excretion can be sought on protein-containing plates and then isolated. Finally, from a clone with protease activity, the plasmid DNA introduced into this transformant is isolated and, by renewed transformation of a bacterium, is checked to find whether the protease activity is plasmid-linked, that is to say whether the protease activity is coupled to the marker property.

Besides the vector DNA with known restriction sites, the plasmid isolated in this way contains the desired structural gene for the highly alkaline initial protease to be optimized and other DNA sequences from the donor bacterium, which are, however, not required here. One example of a vector of this type, called pCLEAN0, is depicted in the restriction map in FIG. 2.

In order to minimize the work involved in the subsequent sequencing of the structural gene of the highly alkaline protease which is to be optimized, it is advisable, before the actual sequencing, to eliminate the additional, unneeded DNA sequences from the donor DNA sequence, and to reduce the donor DNA sequence essentially to the structural gene for the protease. For this purpose, for example the plasmid which comprises the structural gene and the additional DNA sequence is cut (restricted) with a number of different restriction endonucleases, the resulting DNA fragments are separated according to size by gel electrophoresis, and a restriction map is constructed on the basis of the pattern of bands found. The restriction sites located in the region of the donor DNA sequence are determined in this way. Knowledge of the restriction map of the plasmid now makes it possible to cut out of the latter, by cutting with selected restriction endonucleases, a DNA fragment from the donor DNA sequence which now essentially comprises only the structural gene for the highly alkaline protease, the relevant pre and pro units, and the promoter unit required for gene expression.

Reincorporation of this donor DNA sequence which has been reduced in size into a suitable vector makes it possible to obtain a novel vector which is capable of replication and whose ability to express the highly alkaline initial protease can be checked by transforming a bacterium, especially a Bacillus species, with this vector, and cultivating the resulting transformant and checking for protease activity. One example of a reduced vector of this type, called pCLEAN4, is depicted in the restriction map in FIG. 3.

To determine the nucleotide sequence (sequencing) of the protease structural gene, initially the vector described above is replicated in a suitable microorganism, and the protease gene is isolated. The latter is then subcloned into a phagemid, and the resulting phagemids are subsequently transformed into a suitable microorganism, for example *E. coli*, and single-stranded DNA containing the protease gene is produced by cultivating the transformants. The resulting single-stranded DNA is isolated and subjected to sequencing. The sequencing is carried out by known methods, for example, by subjecting the single-stranded DNA with the protease gene to a base-specific partial chemical cleavage by the method of Maxam and Gilbert, *Methods in Enzymology*, Grossmann L. and Moldave K. eds., Academic Press Inc., New York, Vol. 65, p. 499 (1980) or, for example, by employing the single-stranded DNA with the protease gene as a template for the partial synthesis of portions of the complementary DNA strand by the dideoxy chain terminator method of Sanger and Brownlee, *Proc. Natl. Acad. Sci. USA*, Vol. 74, p. 5473 (1977).

The determined nucleotide sequence can now be translated using the genetic code (one triplet word=codon stands for a defined amino acid) into the amino-acid sequence of the protease. To establish the starting point of the amino-acid sequence of the mature protease enzyme (that is to say the enzyme without the pre and pro units), a short piece of the amino-acid sequence at the N-terminal end of the mature protease is determined by known methods for the determination of amino-acid sequences in peptides. The known N-terminal amino-acid sequence can now be assigned, on the basis of the genetic code, to the appropriate portion of the above nucleotide sequence and thus the starting point of the DNA sequence coding for the mature protease can be established. The subsequent amino-acid sequence of the protease then emerges unambiguously from the DNA sequence by assignment of the subsequent amino acids using the genetic code.

According to the invention, the DNA sequence coding for the protease is mutated by replacing the appropriate codons in such a way that the mutated DNA sequence codes for an optimized highly alkaline protease in which the relevant amino acid in at least one of the positions 18, 27, 42, 49, 57, 96, 107, 114, 115, 135, 138, 166, 176, 179, 188, 189, 198, 238, 255, 259, 266 of the amino-acid sequence in FIG. 1, (SEQ. ID. NO. 2) preferably 18, 27, 42, 57, 96, 107, 114, 115, 135, 138, 166, 238, 255, 259, 266, or in one of the positions homologous thereto, has been replaced by a more strongly basic amino acid.

The amino acids which can be replaced according to the invention are located in such positions in surface regions of the protease molecule that the replacement has virtually no effect on the catalytic center of the protease or on centers which are important for maintaining the secondary and tertiary structure of the protease molecule.

In this way, optimized highly alkaline proteases with pH optima from 10 to 12.5 are prepared according to the invention and have, for example, a pH stability which is unchanged from that of the initial protease but have improved washing properties under specific conditions (detergent types, temperature etc.).

The introduction of the point mutations into the DNA coding for the highly alkaline proteases is effected by known methods for directed mutagenesis. For this purpose, circular single-stranded DNA which contains the complete structural gene, or else preferably only that part (for example only the N-terminal part or the C-terminal part) of the structural gene of the original protease in which the mutation is to be carried out, is generated from suitable vectors (phagemids), for example from pCLMUTN1 in FIG. 5 or pCLMUTC1 in FIG. 6, optionally with the assistance of a helper phage. This circular single-stranded DNA is hybridized with a synthetic oligonucleotide which is capable of hybridization and which contains in the desired point mutation site a nucleotide unit which is selected such that the relevant codon codes for an amino acid which is more strongly basic than the original amino acid in this position, for example for arginine or lysine. In addition, the oligonucleotide is also modified, compared to the original nucleotide sequence to be hybridized, by one or a few other nucleotide units, in such a way that although the coding of the original amino-acid sequence remains within the scope of the degeneracy of the genetic code, a restriction site which is present where appropriate in the original protease nucleotide sequence has been deleted in the synthetic oligonucleotide, or another restriction site has been introduced into the synthetic oligonucleotide. The deleted or introduced restriction site is subsequently used for identifying the mutant DNA sequence from the initial DNA sequence using suitable restriction endonucleases. In one variant, in the process of directed mutagenesis, uracilated single-stranded DNA is generated as a template and used for the hybridization with the synthetic oligonucleotides. After the reactions of the process of directed mutagenesis are complete, the uracil-containing DNA single strand which was used as template for generating mutated DNA strands (vectors) can be removed by treatment with uracil N-glucosylase without the need for phenotypic selection of mutants. The glucosylase treatment can be carried out both with the isolated enzyme and using a suitable microorganism which has uracil N-glucosylase activity and has been transformed with mutated vector DNA.

The partially double-stranded DNA sequence obtained by hybridization is then made up to the complete double strand by adding the required nucleotides and exposing to DNA polymerase and DNA ligase. The resulting circular double-stranded DNA sequence is subsequently transformed as vector into a suitable microorganism and, after adequate replication, the mutated DNA sequences are identified via the unique restriction endonuclease recognition sites and subsequently isolated. If uracylated single-stranded DNA is employed, the replication is carried out, for example, in an *E. coli* strain which replicates preferably the mutated, non-uracylated DNA strand of the double-stranded vector generated in the mutation process. This additionally facilitates the selection of the mutated DNA vectors.

The synthetic oligonucleotides needed for the directed mutagenesis are prepared by known methods. For example, the oligonucleotides can be prepared by the method of Beaucage S. L. and Caruthers M. H., *Tetrahedron Letters*, Vol. 22, pp. 1859-1862 (1981) with $\beta$-cyanoethyl phosphoramidite in a Cyclone synthesizer (Biosearch). The resulting oligonucleotides can be purified, for example, by elution from polyacrylamide gels and, where appropriate, subsequent desalting using Sephadex columns and then used further. The synthetic oligonucleotides can be used directly as primers for DNA polymerase in the mutagenesis process described above. The synthetic oligonucleotide sequences comprise, for example, 20 to 30 nucleotide units which code for about 7 to 10 amino acids. Of course, it is also possible to employ longer nucleotide sequences for the above hybridization, but this yields no further advantages as long as adequate ability of the short-chain synthetic oligonucleotides to hybridize is ensured. However, longer nucleotide sequences become suitable in particular when two or more mutations are to be introduced in adjacent positions. The oligonucleotide can then be either synthesized as such from mononucleotides or prepared by synthesis from suitable shorter oligonucleotide sequences. However, this is not absolutely necessary because two or more mutations can also be carried out by consecutive mutations, for example in the N-terminal or in the C-terminal part of the protease DNA, with two or more suitable oligonucleotide sequences. Furthermore, double mutations can also be generated by combination of mutated C-terminal and mutated N-terminal DNA fragments which code for the C-terminal and N-terminal ends, respectively, of a highly alkaline protease according to the invention.

The circular, double-stranded DNA sequences with the introduced mutations which are obtained by the process of directed mutagenesis described above represent mutated vectors from which the complete mutated protease structural gene or the mutated portion of the protease structural gene, depending on the case, can be cut out by treatment with suitable restriction endonucleases and introduced into a suitable expression vector (subcloned). This expression vector can then be used to transform suitable microorganisms, for example Bacillus species, which are subsequently cultivated under suitable conditions for the expression and recovery of the mutated highly alkaline proteases.

In a preferred embodiment of the invention, the complete structural gene is not employed for the directed mutagenesis. Instead, only a portion of the gene in which the mutation is to be generated, is used. For this purpose, for example the N-terminal or C-terminal half of the structural gene is cut with suitable restriction endonucleases, out of the vector which is used for the replication of the structural genes and is subcloned into an appropriate phagemid. This results in vectors which contain either the N-terminal or the C-terminal half of the structural gene of the protease and which are initially sufficiently replicated in a suitable microorganism, for example *E. coli*, and then subjected to the directed mutagenesis described above. Mutagenesis of portions of the structural gene has the advantage that shorter single-stranded DNA sequences can be used and thus considerably fewer nucleotides than when using the complete DNA sequence have to be made up in the partial DNA double strand after the hybridization step with synthetic oligonucleotides. This reduces the synthetic work and, moreover, the risk of undesired chance mutations. Furthermore, it is easy to generate double mutations in the protease DNA sequence by subsequent combination of mutated N- and C-terminal halves of the protease DNA sequence.

The mutated DNA sequences can be cut by suitable restriction endonucleases, out of the cloning vectors used for generating the mutations and be incorporated into vectors which have appropriate restriction sites and represent precursors of the actual expression vectors required for the expression of the highly alkaline protease. These vectors are constructed in such a way that, besides the suitable restriction sites (for example from a synthetic linker), they also already contain the regulatory sequences, signal sequences, promoter sequences and the DNA sequences coding for the pre and pro units of the protease, which are required for the protease expression in a host organism.

Subcloning of a mutated DNA sequence into a vector of this type results in the actual expression vector for an optimized highly alkaline protease. Incorporation of the mutated DNA sequence into this precursor of the expression vector is carried out in such a way that an expression vector with a suitable reading frame is produced. In this connection, it is possible to incorporate mutated portions of the DNA sequence coding for the protease, for example a C-terminal or an N-terminal portion, into vectors already containing the remaining non-mutated or else, where appropriate, mutated (generation of multiple mutations) portion in each case; or the complete mutated DNA sequence coding for the protease is incorporated into vectors which do not yet contain portions of this protease DNA sequence. Examples of such precursor vectors of an expression vector which already contain a portion of the non-mutated or else, where appropriate, already mutated DNA sequence are the vectors called pAL1N and pAL1C whose restriction maps are depicted in FIG. 12 and FIG. 13, respectively. A vector which does not yet contain a portion of the protease DNA sequence is the vector pAL1P with the restriction map indicated in FIG. 11.

The expression vector precursors for the preferred variant of the invention (mutation in the N-terminal half or in the C-terminal half) are obtained as follows, for example. First, a polycloning site is introduced into a Bacillus plasmid. The resulting plasmid is restricted and recombined with an *E. coli* plasmid fragment which contains markers and part-sequences important for replication. Subsequently, where appropriate those restriction sites which would interfere with subsequent process steps are deleted, for example by directed mutagenesis. The resulting plasmid is used to construct a novel vector which contains the DNA sequences from the Bacillus plasmid and the *E. coli* plasmid used for replication, DNA sequences for the promoter, DNA sequences which code for the pre-pro sequence of the protease (for example obtained from the plasmid pCLEAN4 in FIG. 3) and a synthetic linker. One example of a plasmid of this type, called pAL1P, is depicted by the restriction map in FIG. 11. In this case the synthetic linker is selected so that, after cutting with suitable restriction endonucleases, combination if possible either with the complete original structural gene or with the complete mutated structural gene or with mutated or non-mutated portions of the structural gene. To prepare an expression vector precursor which is intended, for example, for recombination with a mutated N-terminal half of the structural gene, for example first the non-mutated or else, where appropriate, an already mutated (for example for generating proteases with mutations in the C- and N-terminal parts of the protease DNA sequence) C-terminal half of the structural gene of the protease is introduced into the vector which has been constructed above and contains the said Bacillus sequences, *E. coli* sequences, the promoter sequences and the pre and pro sequences of the protease, plus the synthetic linker, by cutting the synthetic linker. This results in the aforementioned vectors of the pAL1C type in FIG. 13. Subsequently, the mutated N-terminal half of the protease structural gene which is still missing is introduced by cutting the synthetic linker again. A vector of the pAL1NC type in FIG. 14 is obtained in this way. The reverse case is analogous. Then the unmutated, or optionally already mutated, N-terminal half is introduced first into a vector of the pAL1P type in FIG. 13, and subsequently the mutated C-terminal half is introduced into the vector of the pAL1N type in FIG. 12 obtained in this way, likewise resulting in a vector of the pAL1NC type in FIG. 14.

The expression vectors described above are used to transform suitable bacteria, preferably Bacillus species, especially Bacillus subtilis, *Bacillus licheniformis* and *Bacillus alcalophilus*. The transformants are subsequently cultivated in a known manner, and the highly alkaline protease which is produced is isolated from the culture medium. For this purpose, the expression vectors can be transformed both into bacteria which are still able to produce their own protease and into protease-deficient bacteria (which no longer produce their own protease). In the case of host organisms producing their own protease, the produced own protease can be removed, if desired, from the highly alkaline protease according to the invention by subsequent purification operations, for example by high-resolution liquid chromatography (HPLC). By contrast, a purification step of this type can be omitted in the case of protease-deficient host organisms because the latter are only able to produce (or essentially only able to produce) the protease according to the invention.

The following disclosure describes typical exemplary embodiments of the invention, in order to explain the invention further but without thereby restricting the invention.

In order to simplify the examples, some frequently recurring methods and terms are explained in detail hereinafter and then merely referred to by a short designation in the individual examples. Unless indicated otherwise, in general the methods used were those described in Maniatis et al., *Molecular Cloning, A Laboratory Manual*, Cold Spring Harbor Laboratory, (1982).

The initial vectors used herein are commercially available on an unrestricted basis; or they can be prepared from available vectors by known methods.

The various restriction endonucleases used are state of the art and commercially available. The reaction, cofactor and other conditions required in each case when these known restriction endonucleases are used are likewise known. For example, one unit ($=1U=$unit) of the restriction endonuclease can be employed in about 20 $\mu$l of a buffer solution for an amount of about 1 $\mu$g of a vector or of a DNA fragment. Adequate incubation times of about one hour at 37° C. were usually observed, but the incubation conditions can be adjusted to suit the given requirements. After incubation with a restriction endonuclease, the protein was removed by extraction (for example with phenol and chloroform), and the cut DNA was isolated (for example from the aqueous fraction by precipitation with ethanol) and then used further.

The cutting of vectors with restriction endonucleases can, where appropriate, be followed by hydrolysis of the terminal 5'-phosphate residue with an alkaline phosphatase (dephosphorylation). It is possible in this way to prevent self-ligation of the ends, which have been produced in the cutting, of the restricted DNA or of the restricted vector, which would prevent the desired insertion of a foreign DNA fragment into the restriction site. Where a dephosphorylation of the 5' end was carried out in the examples, this was carried out in a known manner. Other details of the procedure for dephosphorylation and reagents required therefor can be found in Maniatis et al. (pp. 133–134).

Partial hydrolysis means incomplete digestion of DNA by a restriction endonuclease. In this case the reaction conditions are selected such that a DNA substrate is cut at some but not all recognition sites for the restriction endonuclease employed.

To obtain and isolate particular DNA fragments, for example after treatment of DNA with restriction endonucleases, the resulting DNA fragments were separated in a known manner by gel electrophoresis (for example on agarose gel) and subsequently identified via the molecular weight (determination by comparison with reference DNA fragments of known molecular weight), and the desired DNA fragments were removed from the appropriate gel zones.

Treatment with the Klenow fragment of DNA polymerase I from *E. coli* means a process for filling in the inner 3'ends of double-stranded DNA with nucleotides which are complementary to the nucleotides in the particular protruding 5' ends of the DNA double strand. This process is used, for example, when inner DNA strand ends which result from a cleavage of double-stranded DNA with restriction endonucleases are to be filled in with nucleotides, for example in order to generate blunt DNA double-stranded ends required for further ligations. The treatment with the Klenow fragment is carried out by allowing the DNA which is to be filled in to react with the suitable complementary nucleotides in the presence of a sufficient catalytic activity of the Klenow fragment of *E. coli* DNA polymerase I (for example at 15° C. for about 15 min). The Klenow fragment and other reagents required for the Klenow treatment are known in the prior art and are commercially available. Further details of the Klenow treatment can be taken, for example, from Maniatis et al. (pp. 107–108).

Ligation means a process for forming phosphodiester linkages between DNA fragments (see, for example, Maniatis et al., p. 146). Ligations can be carried out under known conditions, for example in a buffer containing about 10 units of T4 DNA ligase per 0.5 μg of an approximately equal molar amount of the DNA fragments to be ligated.

Transformation means the insertion of DNA into a microorganism so that the DNA can be replicated and expressed therein. Suitable for transformation of *E. coli* is, for example, the calcium chloride method of Mandel et al., *J. Mol. Biol.*, Vol. 53, p. 154 (1970) or of Maniatis et al. (pp. 250–251). The method Anagnostopolous et al., *J. Bact.*, Vol. 81, pp. 791–746 (1961) is suitable, for example, for Bacillus species.

A linker is a short-chain double-stranded DNA fragment which has some recognition sites for restriction endonucleases and is suitable for joining DNA fragments. Linkers are employed, for example, in the recombination of DNA fragments to give a vector and can be used to introduce particular recognition sites for restriction endonucleases into this vector.

A polycloning site (polylinker) is a short to medium double-stranded DNA fragment which has in close proximity a plurality of recognition sites for restriction endonucleases. One polycloning site which is used in the examples and derives from the vector M13tg131 has, for example, a size of about 0,07 KB (kilobase pairs) and has recognition sites for 14 different restriction endonucleases.

The *Bacillus alcalophilus* strain employed in Example 1 and called *Bacillus alcalophilus* HA1 was deposited at the Deutsche Sammlung yon Mikroorganismen (DSM) with the DSM number 5466 on Jul. 28, 1989.

Brief Description of the Drawings

FIG. 1 shows the DNA sequence (SEQ. ID. NO. 1) of the AvaI/HindIII fragment with the structural gene of the highly alkaline initial protease from Bacillus alcalophilus HA1, and the amino-acid sequence of this initial protease.

FIG. 4 shows the DNA sequences for the synthetic oligonucleotides I–XV (SEQ. ID. NOS. 13–17) and indicates eliminated and generated recognition sites for individual restriction endonucleases; the nucleotide alterations generated compared to the original DNA sequence of the initial protease are identified by indicating the altered nucleotides with small letters.

EXAMPLE 1

Preparation of a genomic DNA library from *B. alcalophilus* and isolation of the gene for the highly alkaline initial protease Chromosomal DNA was isolated by the method of Saito et al., *Biochim. Biophys. Acta.*, Vol. 72, pp. 619–629 (1963) from the natural isolate *Bacillus alcalophilus* HA1 (DSM 5466) and was partially hydrolyzed with the restriction endonuclease Sau3A. The restriction fragments were fractionated by electrophoresis on an agarose gel, and the fragments with a size of 3 to 8 kilobases (KB) were isolated.

The isolated and size-selected DNA fragments from *Bacillus alcalophilus* HA1 were subjected to in vitro recombination with vector DNA from the plasmid pUB110 (preparation as described in Example 9).

For this, the plasmid pUB110 was first restricted with the restriction endonuclease BamHI and subsequently dephosphorylated with alkaline phosphatase from calf intestine. Subsequently 2 μg of the restricted and dephosphorylated vector DNA were incubated with 8 μg of the *B. alcalophilus* DNA fragments in a total volume of 100 μl with T4 DNA ligase at 16° C. for 24 hours.

Figure 2:
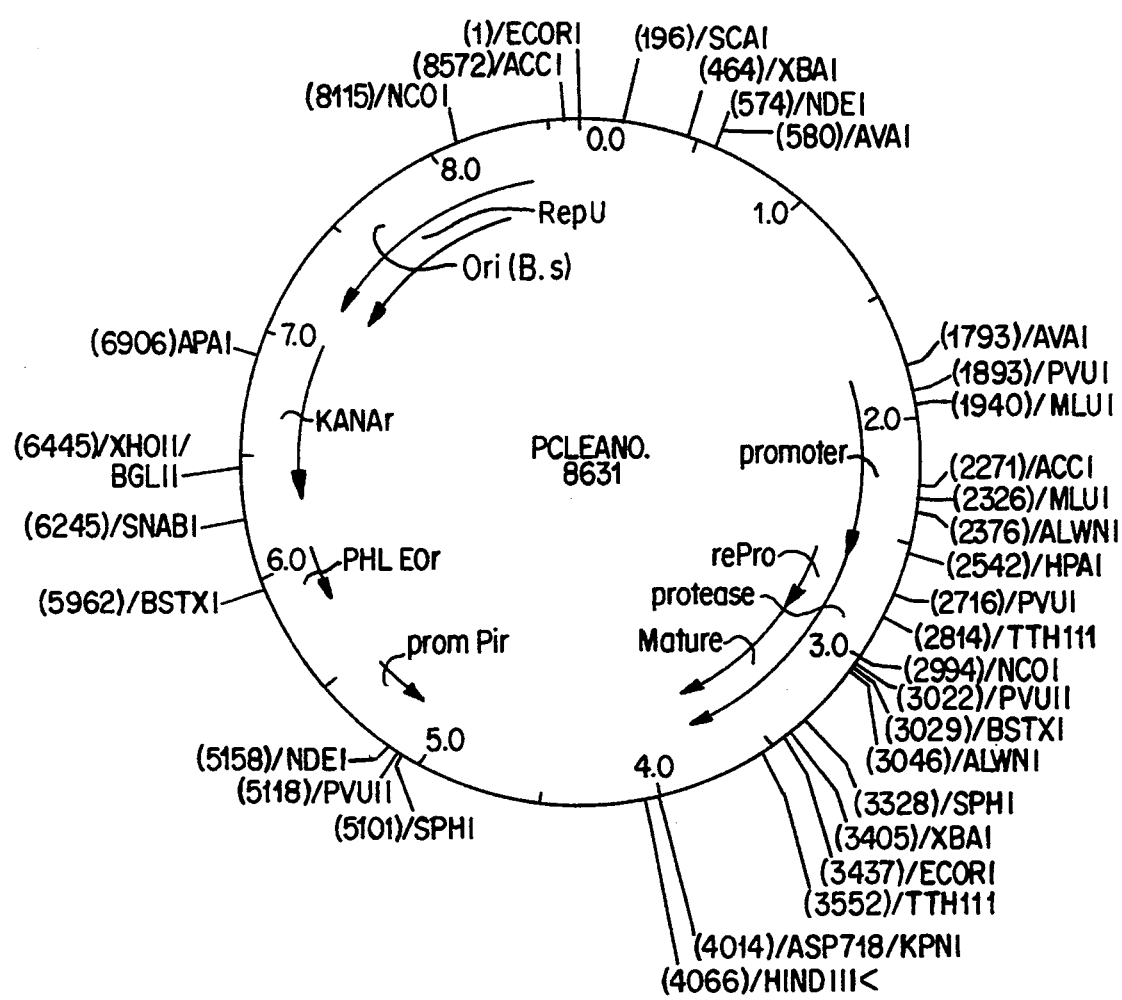
FIG. 2 shows the restriction map of the plasmid pCLEAN0.

The resulting in vitro recombined DNA was used to transform protoplasts of the strain Bacillus subtilis BD224 (Bacillus Genetic Stock Center 1 A 46) by the method described by S. Chang and N. Cohen, *Mol. Gen. Genet.*, Vol. 168, pp. 111–115 (1979). The transformants were selected on plates with neomycin and subsequently transferred to skimmed milk agar. Among 13,800 transformants examined, one which formed a distinctly larger zone due to proteolysis of the skimmed milk agar was found. The plasmid DNA was isolated from this clone by the method of Maniatis et al. The cloned fragment of *B. alcalophilus* DNA contained in this plasmid had a size of 4.1 KB and contained (as was demonstrated in Example 2) the complete correct DNA sequence for the highly alkaline protease from *Bacillus alcalophilus* HA1. The plasmid was called pCLEAN0. The plasmid pCLEAN0 was cut with various restriction endonucleases, the restricted DNA was fractionated by electrophoresis on an agarose gel, and a restriction map was drawn up on the basis of the pattern of bands and was subsequently checked against the sequencing result from Example 4. The restriction map of this plasmid is depicted in FIG. 2.

EXAMPLE 2

Expression of the structural gene and determination of the proteolytic activity of the expressed initial protease The plasmid pCLEAN0 underwent renewed introduction into the strain *B. subtilis* BD224, and the resulting transformants were cultivated. A *B. subtilis* BD224 transformed with the plasmid pUB110, and the initial strain for the isolation of the protease gene, the *B. alcalophilus* HA1, were likewise cultivated as control strains. For this purpose, the strain *B. subtilis* BD224 (pCLEAN0) and the control strains *B. subtilis* BD224 (pUB110) and *B. alcalophilus* HA1 were incubated in a medium which contained 8 g of nutrient broth, 40 mg of $MgSO_4$, 0.2 g of $CaCl_2$, 1 mg of $MnCl_2$ and 1 mg of $FeSO_4$ per liter at 37° C. and 250 rpm. The medium for the plasmid-containing *B. subtilis* strains additionally contained 10 μg of neomycin/ml. The medium for the alcalophilic initial strain additionally contained 10 ml of sodium carbonate buffer (1 molar, pH 9.75) per liter of medium.

After 28 hours, samples were taken from the cultures and centrifuged, and the proteolytic activities in the supernatants were determined.

Furthermore, the proteolytic activities were also determined in the presence of the serine protease inhibitor PMSF (phenylmethylsulfonyl fluoride) and the metalloprotease inhibitor EDTA (ethylenediaminetetraacetic acid).

Table 1 shows the results in the absence of inhibitors and in the presence of the inhibitors PMSF and EDTA.

TABLE 1

| Supernatant from | Activity in the presence of | | |
|---|---|---|---|
| | — | PMSF | EDTA |
| *B. alcalophilus* HA1 | 100% | 1.5% | 95% |
| *B. subtilis* BD224 (pUB110) | 100% | 44% | 51% |
| *B. subtilis* BD224 (pCLEAN0) | 100% | 6% | 78% |

The determination of proteolytic activities for the culture supernatants obtained above by centrifugation of the culture samples was supplemented by fractionation of the proteins contained in these supernatants by isoelectric focusing. This shows that the strain *B. subtilis* BD224 (pCLEAN0) excretes, in contrast to the control strain (*B. subtilis* BD224 containing only the vector DNA of the plasmid pUB110), a protein which has the same isoelectric point as the highly alkaline protease produced by *B. alcalophilus* HA1.

The production of protease by the *B. subtilis* BD224 transformed with pCLEAN0 confirms that the phenomenological properties, such as neomycin resistance and protease activity (that is to say increased zone formation on skimmed milk agar), used for selecting the protease structural gene in Example 1 are linked to the same plasmid pCLEAN0. The results furthermore show that the DNA fragment from *B. alcalophilus* HA1 contained in the plasmid pCLEAN0 contains the complete information for the synthesis of the highly alkaline *B. alcalophilus* protease because the protease produced by *B. subtilis* BD224 (pCLEAN0) has the same isoelectric point as the original *B. alcalophilus* HA1 protease and, moreover, behaves analogously to *B. alcalophilus* protease towards inhibitors such as PMSF or EDTA.

EXAMPLE 3

Construction of the plasmid pCLEAN4

Plasmid pCLEAN0 was restricted with the restriction endonucleases AvaI and HindIII. The DNA fragment 2.3 KB in size was isolated and ligated with the vector pUB131 (preparation as described in Example 10) which had previously likewise been cut with AvaI and HindIII.

Figure 3:
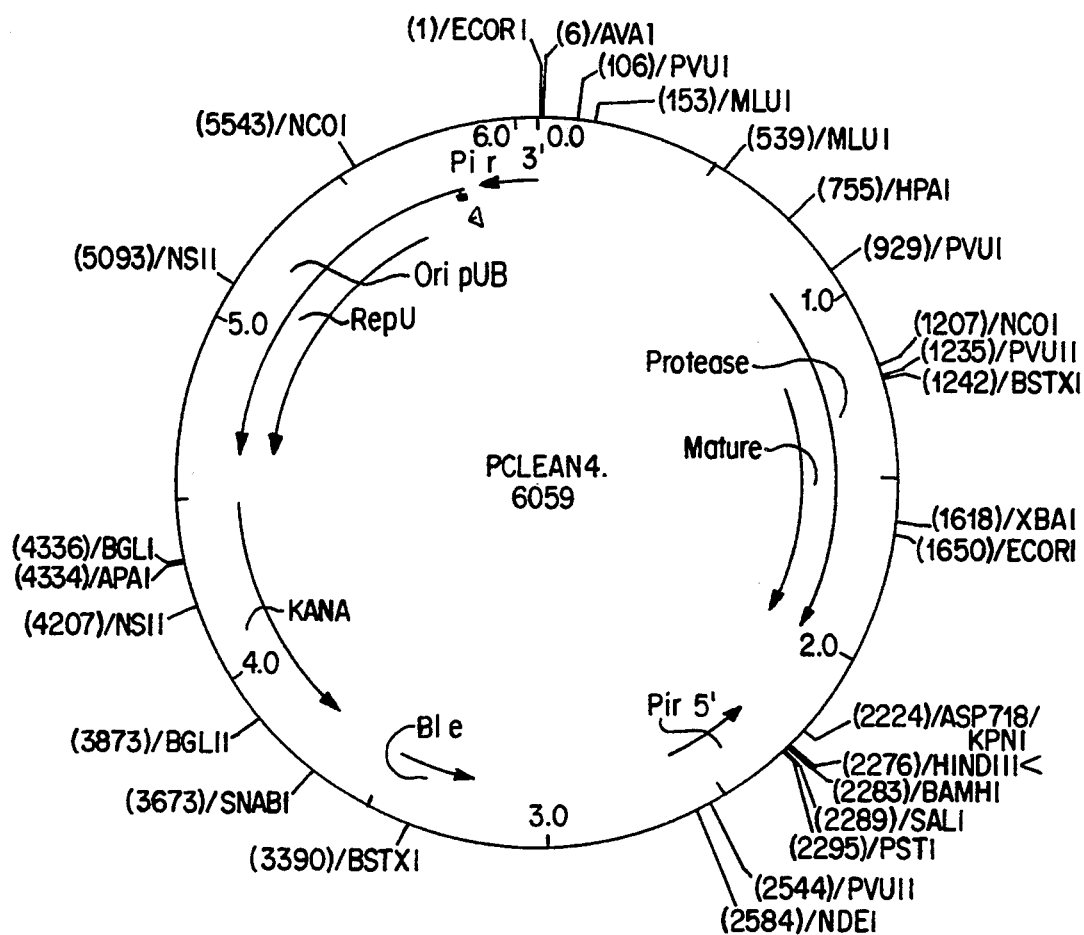
FIG. 3 shows the restriction map of the plasmid pCLEAN4.

The resulting plasmid, which was called pCLEAN4, was introduced into the strain *B. subtilis* BD224. The transformants were able to excrete the highly alkaline protease, which shows that the AvaI/HindIII fragment contains the complete structural gene for the highly alkaline protease from *B. alcalophilus* HA1. The restriction map of the plasmid pCLEAN4 is depicted in FIG. 3.

EXAMPLE 4

Sequencing of the structural gene for the highly alkaline protease

To prepare single-stranded DNA of the protease structural gene, the plasmid pCLEAN4 was cut with the restriction endonucleases AvaI and HindIII, and the AvaI/HindIII DNA fragment about 2.3 KB (protease structural gene) was introduced into the phagemids pBS (+) or pBS (−); the phagemids pBS (±) were purchased from Stratagene (La Jolla, Calif.). The nucleotide sequence of the protease gene contained in the isolated single-stranded phagemids was determined by the dideoxy chain-terminator method of Sanger et al., *Proc. Natl. Acad. Sci. USA*, Vol. 74, pp. 5473 (1977) and the method of base- specific chemical cleavage of the DNA single strand of Maxam et al., *Methods in Enzymology*, Grossmann L., Moldave K., eds., Academic Press Inc., New York, Vol. 65, p. 499 (1980). The nucleotide sequence (SEQ. ID. NO. 1) which was found, and the assigned amino-acid sequence of the protease, are depicted in FIG. 1 (SEQ. ID. NO. 2). The start of the amino-acid sequence of the mature highly alkaline protease in position 1190 of the nucleotide sequence was determined by amino-acid sequencing of the N-terminal end of the highly alkaline protease.

EXAMPLE 5

Preparation of mutated DNA sequences by directed mutagenesis

The directed mutations were carried out in DNA part sequences of the protease structural gene by the primer extension technique described by T. A. Kunkel, *Proc. Natl. Acad. Sci. USA*, Vol. 82, pp. 488–492 (1985). Employed for this were the plasmids pCLMUTN1 (prepared as described in Example 6) and pCLMUTC1 (prepared as described in Example 7) which were initially converted into their uracilated, single-stranded analogs as described hereinafter. The initial vectors pCLMUTN1 and pCLMUTC1 do not contain the complete DNA sequence of the protease structural gene from *B. alcalophilus* HA1; they contain only the N-terminal half (pCLMUTN1) or the C-terminal half (pCLMUTC1) thereof.

These vectors are, as derivatives of a phagemid, capable to a certain extent of forming single-stranded vector DNA which, under the conditions given here, could be expelled and isolated from the host organism used for the replication.

Each of these vectors was introduced into *E. coli* CJ236 as host organism using the $CaCl_2$ method of Maniatis et al. (pp. 250–251).

Since, on replication of vectors, the bacterium *E. coli* CJ236 (mutant deficient in uracil N-glycosylase) incorporates the nucleotide uracil in place of thymine in the DNA sequence of the vector, cultivation of the aforementioned transformants results in the uracil containing analogs of the vector pCLMUTN1 or pCLMUTC1. These uracil-containing vectors are indistinguishable in in vitro reactions from the usual thymine-containing vectors. The uracil content in the vector DNA does not interfere with in vitro DNA syntheses because uracil is not mutagenic either in vitro or in vivo, and uracil codes in the same way as thymine. Uracilated vectors can be employed advantageously for the subsequent in vitro reactions of directed mutagenesis. After the reactions are complete, the uracil-containing DNA single strand which has been used as template for generating mutated DNA strands (vectors) can be removed by treatment with uracil N-glycosylase without the need for phenotypic selection of mutants. The glycosylase treatment can be carried out both with the isolated enzyme and with an $E. coli$ strain which has been transformed with vector DNA and has uracil N-glycosylase activity.

The uracilated single-stranded DNA of the vectors pCLMUTN1 and pCLMUTC1 required as template for the directed mutagenesis was prepared by cultivating $E. coli$ CJ236 bacteria which had been transformed with one of the two vectors and had additionally been infected with the helper phage M13K07 (Bio-Rad Laboratories, Richmond, Calif.).

The helper phage itself is scarcely capable of replication and displays no interfering interaction with the vector DNA of the vectors pCLMUTN1 or pCLMUTC1. Its task is to synthesize coat proteins for the uracilated single-stranded vector DNA formed. Coated single-stranded vector DNA is expelled from the host organism $E. coli$ CJ236 and can be isolated from the culture medium. The assistance of the helper phage considerably increases the qualitative and quantitative yield of (of uracylated in this case) single-stranded vector DNA.

The isolated, uracilated DNA single-stranded vectors pCLMUTN1 or pCLMUTC1 were hybridized with the synthetic oligonucleotides which were prepared as in Example 8 and contained a mutation site and simultaneously acted as primers for the subsequent making up to the complete DNA double strand with mutation.

The second DNA strand was synthesized by addition of nucleotides with T4 DNA polymerase and subsequent ligation of the newly formed strand with T4 DNA ligase (Kunkel et al., Methods in Enzymol., Vol. 154, pp. 367-382 (1987). The double-stranded vector DNA formed was transformed into $E. coli$ MC1061, and the mutated vectors were identified by checking the appropriate unique restriction endonuclease recognition sites which have been introduced or removed with the synthetic oligonucleotides.

To prepare, for example, two mutations either in the N-terminal or in the C-terminal part of the protease structural gene, the process of this example was, after the introduction of a first mutation (use of a first synthetic oligonucleotide of Example 8) into a part of the protease structural gene, repeated in an analogous manner using another synthetic oligonucleotide of Example 8 for introducing a second mutation into this part of the protease structural gene. This resulted in mutated vectors of the pCLMUTN1 or pCLMUTC1 type with, for example, two mutations either in the N-terminal or in the C-terminal part of the protease structural gene.

EXAMPLE 6

Construction of the vector pCLMUTN1.

Figure 5:
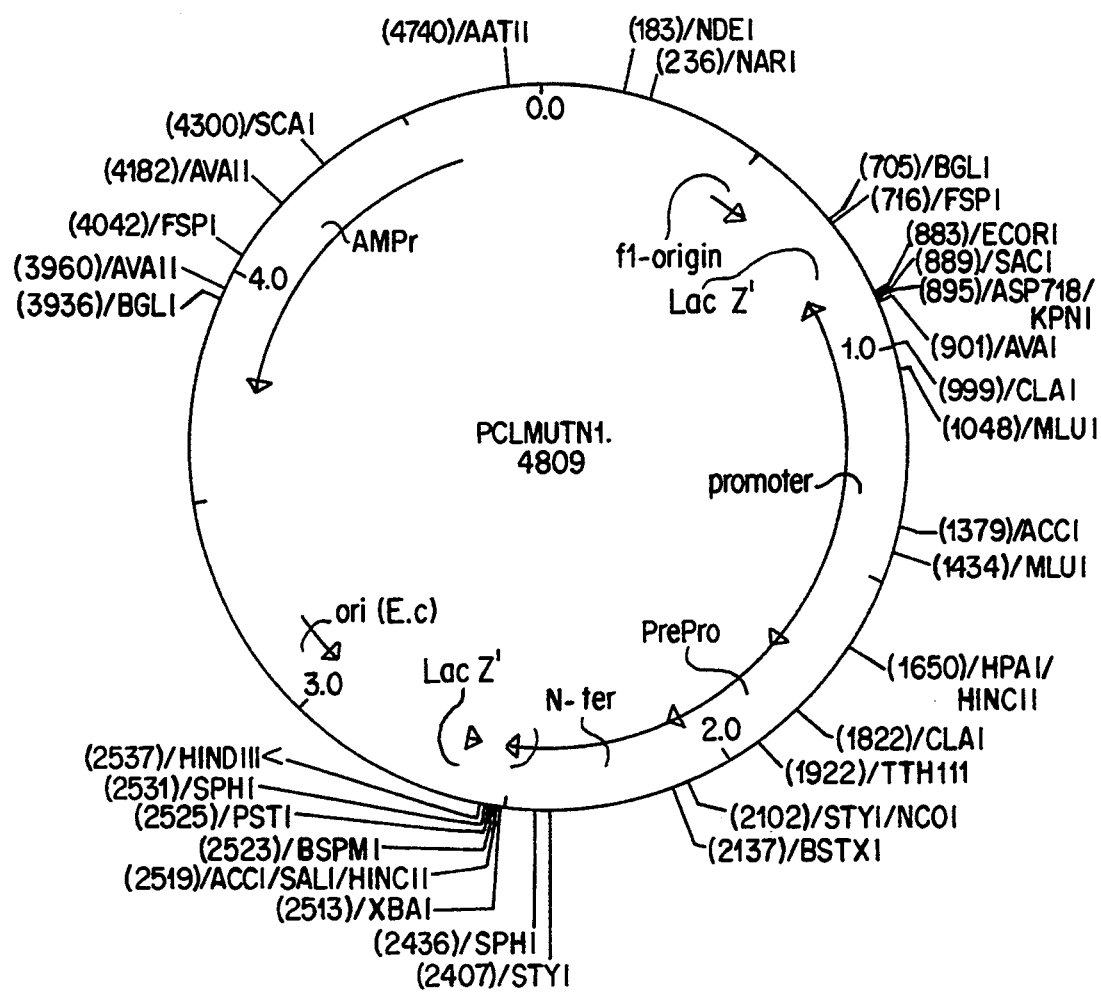
FIG. 5 shows the restriction map of the vector pCLMUTN1.

The plasmid pCLEAN4 prepared in Example 3 was cut with AvaI. The protruding ends ("sticky ends") were filled in by adding the required nucleotides using the Klenow fragment of $E. coli$ DNA polymerase I (Maniatis et al., p. 114) to give the DNA double strand. Subsequent restriction of this DNA with XbaI was followed by isolation of the N-terminal fragment, comprising 1618 base-pairs (BP), of the protease gene and cloning of the isolated fragment into the SmaI/XbaI site of pBS. The resulting vector was called pCLMUTN1. The restriction map of this vector is depicted in FIG. 5.

EXAMPLE 7

Construction of the vector pCLMUTC1

Figure 6:
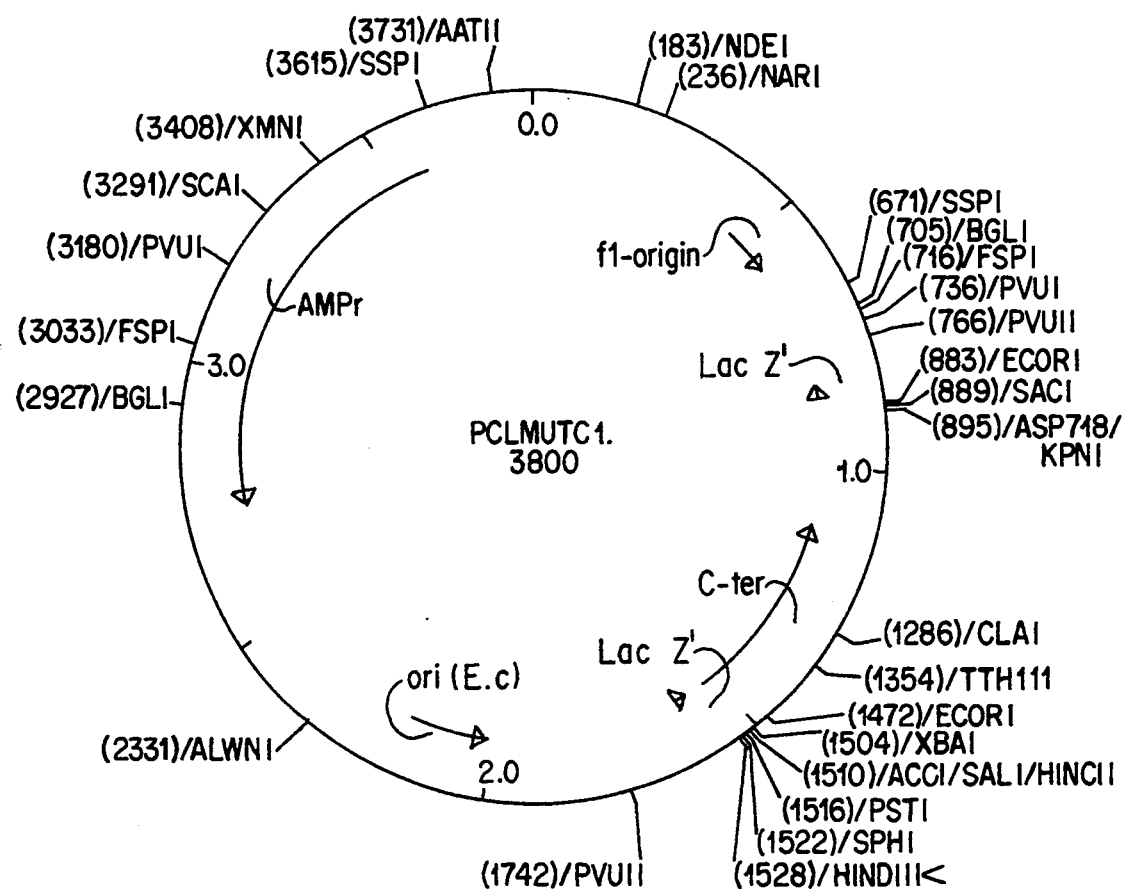
FIG. 6 shows the restriction map of the vector pCLMUTC1.

The plasmid pCLEAN4 prepared in Example 3 was cut with the restriction endonucleases XbaI and Asp718. The XbaI/Asp718 double-stranded DNA fragment which comprises 658 BP and contains the C-terminal half of the protease structural gene was cloned into the XbaI/Asp718 site of pBS. The resulting vector was called pCLMUTC1. The restriction map of this vector is depicted in FIG. 6.

EXAMPLE 8

Synthesis of artificial oligonucleotides for directed mutagenesis

Synthetic oligonucleotides were prepared by the method of S. L. Beaucage and M. H. Caruthers, Tetrahedron Letters, Vol. 22, pp. 1859-1862 (1981) with β-cyanoethyl phosphoramidite in a Cyclone synthesizer (Biosearch). The resulting oligonucleotides were purified by elution from polyacrylamide gels and subsequent desalting using Sephadex G25 columns. Examples of the synthesized nucleotide sequences and their properties are depicted in FIG. 4. The sequences of the synthetic oligonucleotides I to XV (SEQ. ID. NOS. 3-17) which were used in the process of Example 5 for introducing the mutations into the protease gene were selected so that they met the following conditions:

The DNA sequence of the synthetic oligonucleotides was still sufficiently complementary to the corresponding sequence of the protease gene to ensure adequate hybridizability thereof.

Replacement of one or more nucleotides within the codon which codes for the amino acid to be replaced by other nucleotides so that this mutated codon now codes for a more strongly basic amino acid selected from the lysine or arginine group (mutations). The codon employed for the new, more strongly basic amino acid was that which was previously found to be most common in the protease gene for the appropriate, more strongly basic amino acid.

Replacement of other nucleotides within other codons so that although the original coding of the amino acid was retained, the result was that recognition sequences for restriction endonucleases occurring in the protease gene were removed or generated anew. The latter were used in the process of Example 5 to facilitate screening for the vectors with the mutated DNA sequences for the novel highly alkaline proteases.

EXAMPLE 9

Isolation and purification of the plasmid pUB110.

The plasmid pUB110 was isolated by the method of T. J. Gryczan et al., *J. Bacteriol.*, Vol. 34, pp. 318–329 (1978) from the strain *Bacillus subtilis* BD366 (Bacillus Genetic Stock Center 1 E 6) and subsequently purified by cesium chloride density gradient centrifugation by the method of Maniatis et al. (p. 93). The vector pUB110 contains a restriction site, which occurs only once, for the restriction endonuclease BamHI and, as marker, a DNA sequence which codes for resistance to the antibiotic neomycin, as well as DNA sequences required for replication in Bacillus species ("origin of replication").

EXAMPLE 10

Construction of the vector pUB131

Figure 7:
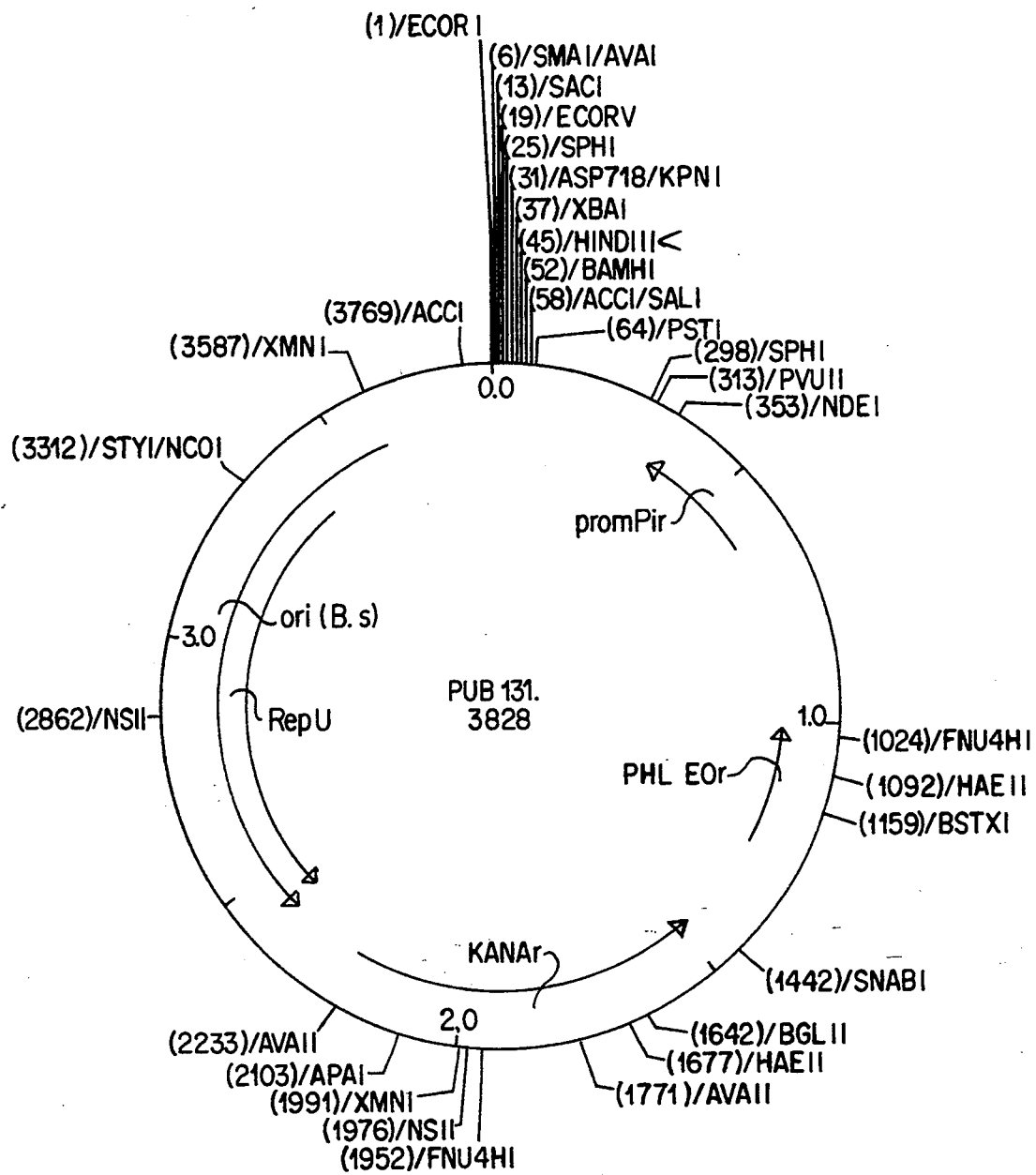
FIG. 7 shows the restriction map of the vector pUB131.

The plasmid pUB110 obtained as in Example 9 was restricted with EcoRI and BamHI. The smaller DNA fragment (790 BP) was replaced by a polylinker which was composed of 67 base-pairs and had previously been isolated as EcoRI/BglII fragment from the vector M13tg131 (Amersham, Buckinghamshire, England). The new vector was called pUB131. The vector pUB131 is thus a derivative of pUB110 in which the EcoRI/BamHI fragment about 0.8 KB in size has been deleted and, in its place, a polycloning site has been incorporated. The restriction map of this vector is depicted in FIG. 7.

EXAMPLE 11

Construction of the vector pUBC131

Figure 8:
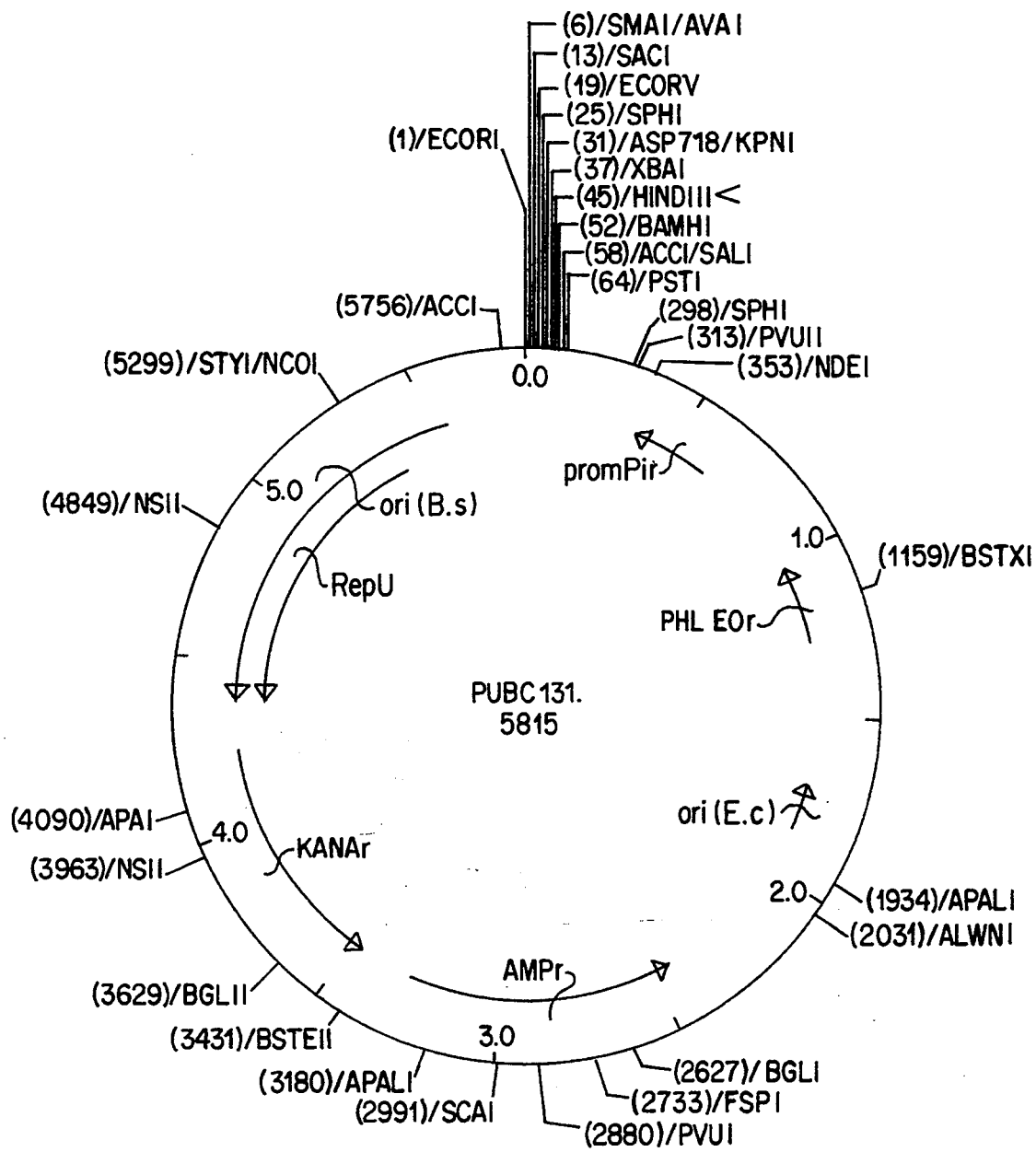
FIG. 8 shows the restriction map of the vector pUBC131.

The plasmid pUC18 (purchased from Pharmacia LKB, Uppsala, Sweden) was cut with AatII and PvuII. The fragment which is 1,990 base-pairs in size and has the β-lactamase gene and the *E. coli* origin of replication was isolated. The protruding ends ("sticky ends") were filled in by addition of the required nucleotides using the Klenow fragment of *E. coli* DNA polymerase I (Maniatis et al., p. 114) to yield the DNA double strand. The fragment was subsequently incorporated into the SnaBI site of the vector pUB131 obtained as in Example 10. The new vector was called pUBC131. The restriction map of this vector is depicted in FIG. 8.

EXAMPLE 12

Construction of the vector pUBC132

Figures 9A, 9B:
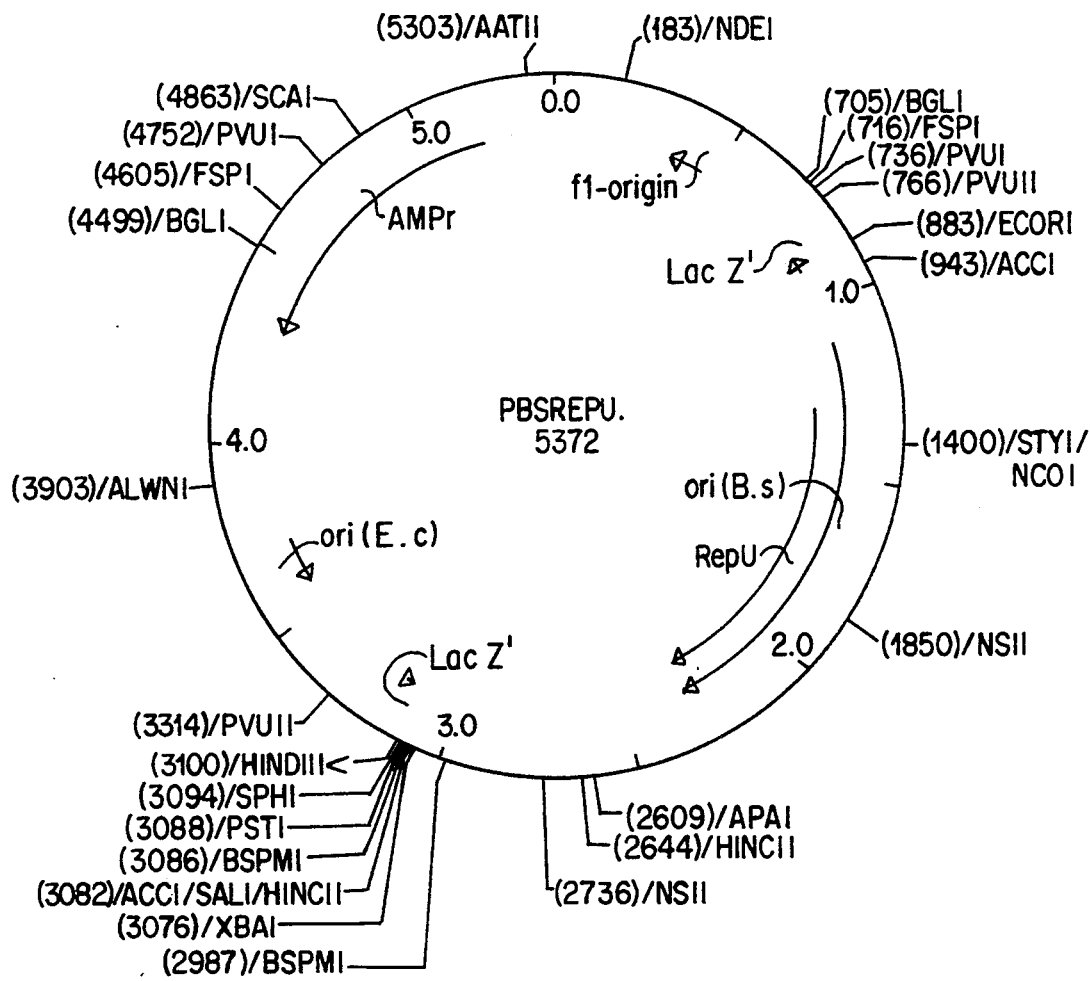
FIG. 9 shows the restriction map of the vector pBSREPU (FIG. 9a) and the synthetic DNA sequence (FIG. 9b) for eliminating the NcoI or StyI recognition site (which is contained in the DNA sequence which codes for the repU protein) from the vector pUBC131.
Figure 10:
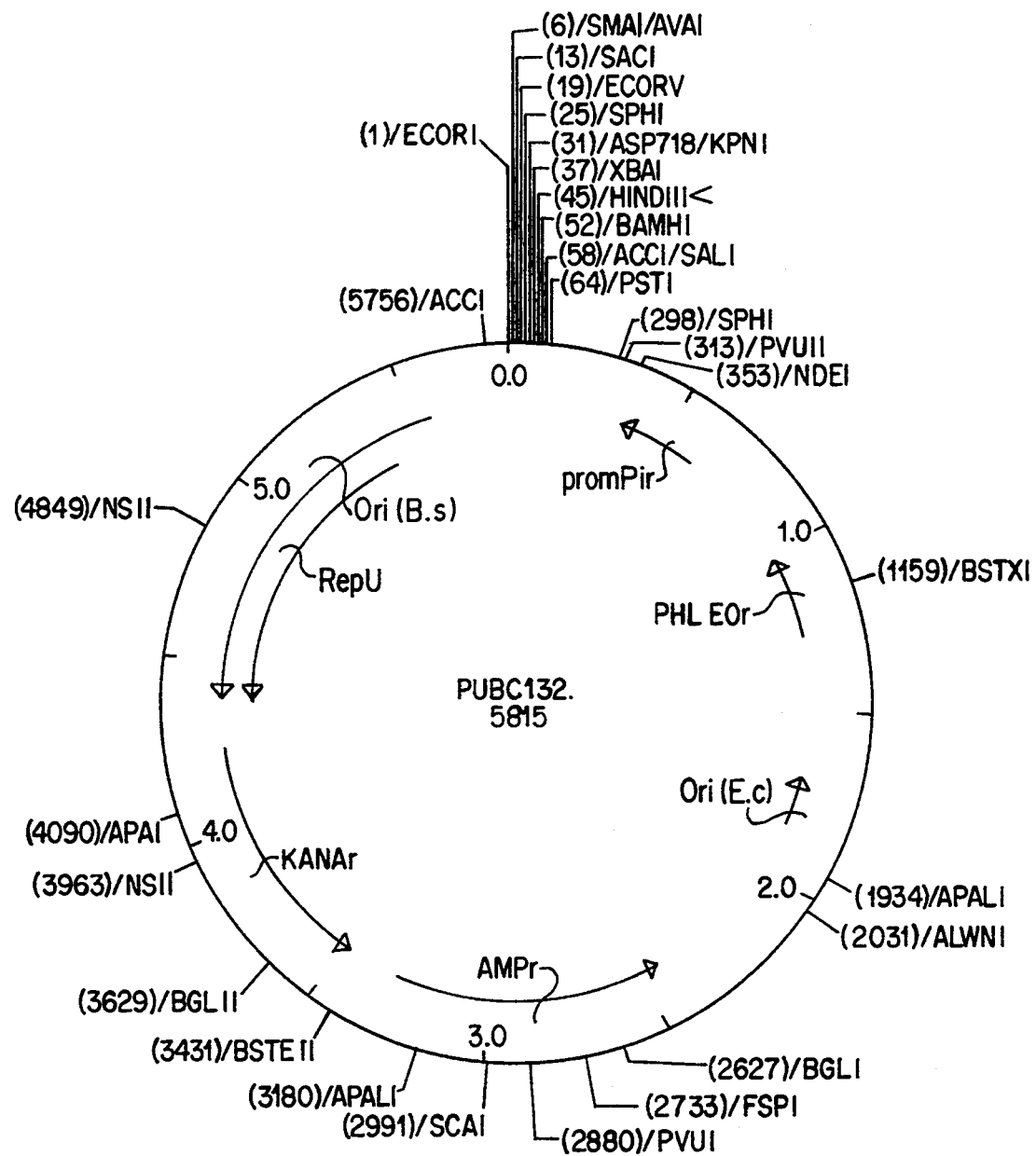
FIG. 10 shows the restriction map of the vector pUBC132.

The 2,187 base pair EcoRI/BglII fragment of the vector pUBC131 obtained in Example 11 was subcloned into the EcoRI/BamHI site of pBS (+). The resulting vector, whose restriction map is depicted in FIG. 9a, was called pBSREPU. Subsequently the NcoI or StyI recognition site which is present in the DNA sequence for the repU polypeptide in the vector pBSREPU (I. Maciag et al., *Mol. Gen. Genet.*, Vol. 212, pp. 232–240 (1988) was eliminated by directed mutagenesis, by replacing the nucleotide sequence CCA TGG by the nucleotide sequence CCG TGG (both nucleotide sequences code for the amino-acid sequence tryptophan-proline). The procedure was analogous to the procedure of Example 5. For this, uracilated single-stranded DNA of the vector pBSREPU was prepared as a template for the directed mutation to eliminate the NcoI or StyI recognition site. This template was subsequently made up to the DNA double-stranded vector in a manner analogous to the primer extension technique described in Example 5, using the synthetic oligonucleotide in FIG. 9b (prepared and purified in a manner analogous to the process for preparing the synthetic oligonucleotides of Example 8), and the vectors which were now free of NcoI and StyI recognition sites were isolated by transformation and cultivation of *E. coli* MC1061. The 1,726 BP EcoRI/ApaI fragment of the isolated vector was introduced into the EcoRI/ApaI site of pUBC131. The new vector, whose restriction map is depicted in FIG. 10, was called pUBC132.

EXAMPLE 13

Construction of the plasmid pAL1P.

Figure 11:
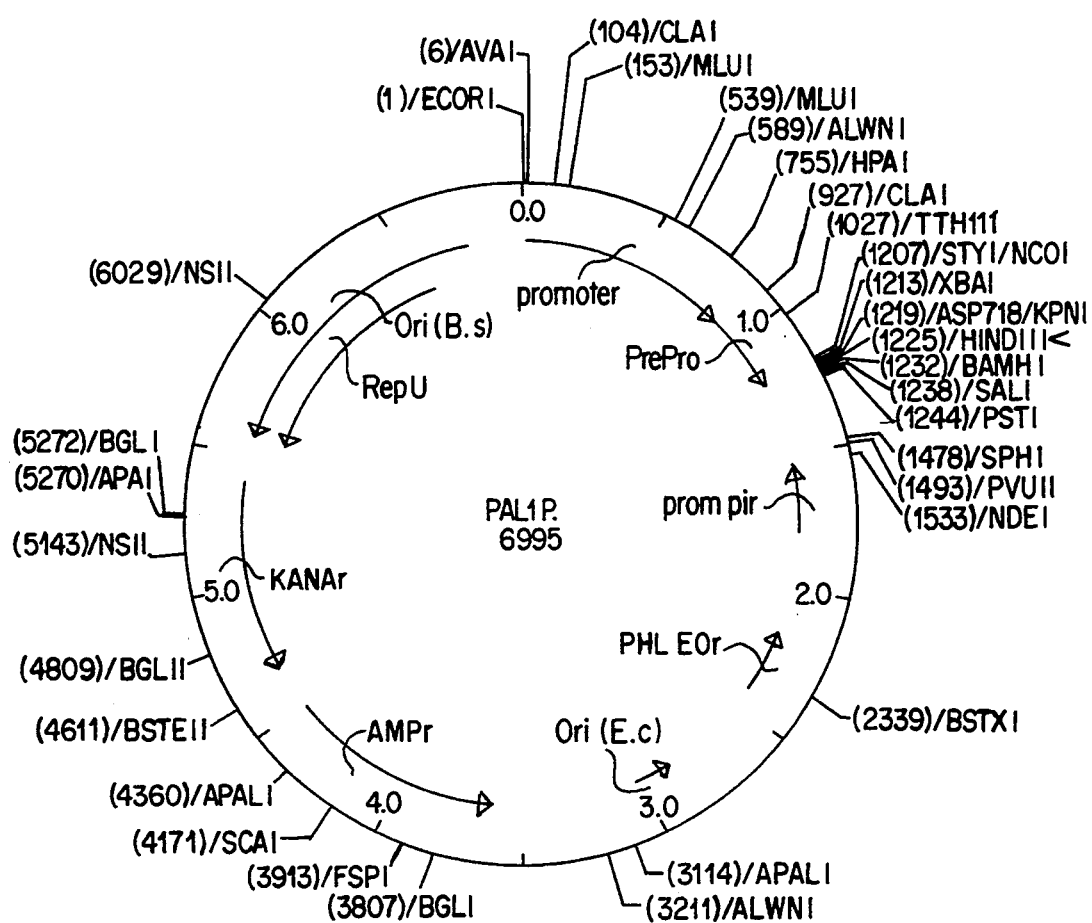
FIG. 11 shows the restriction map of the plasmid pAL1P.

The plasmid pAL1P was prepared by ligation of the following three elements:
- the AvaI/NcoI fragment of pCLEAN4 which is 2,218 base-pairs in size; the fragment contains the promoter and prepro region of the highly alkaline initial protease;
- the synthetic linker prepared in Example 17; this contains single recognition sites for the restriction endonucleases NcoI, XbaI and Asp718 which make it possible to introduce the mutated N-terminal and C-terminal halves of the protease gene from the mutated vectors pCLMUT1 and pCLMUTC1 or to introduce the complete gene of the initial protease from the plasmid pCLEAN4;
- the AvaI/HindIII fragment which is 5776 base-pairs in size from the vector pUBC132 prepared in Example 12; this fragment contains DNA sequences for replication and selectable markers in *E. coli*, as well as DNA sequences for replication and selectable markers in *B. subtilis*, *B. licheniformis* and *B. alcalophilus*. The vector pAL1P was constructed in *E. coli* MC1061, and the vector was isolated from ampicillin resistant *E. coli* transformants. The restriction map of the resulting vector is depicted in FIG. 11.

EXAMPLE 14

Construction of the plasmid pAL1N

Figure 12:
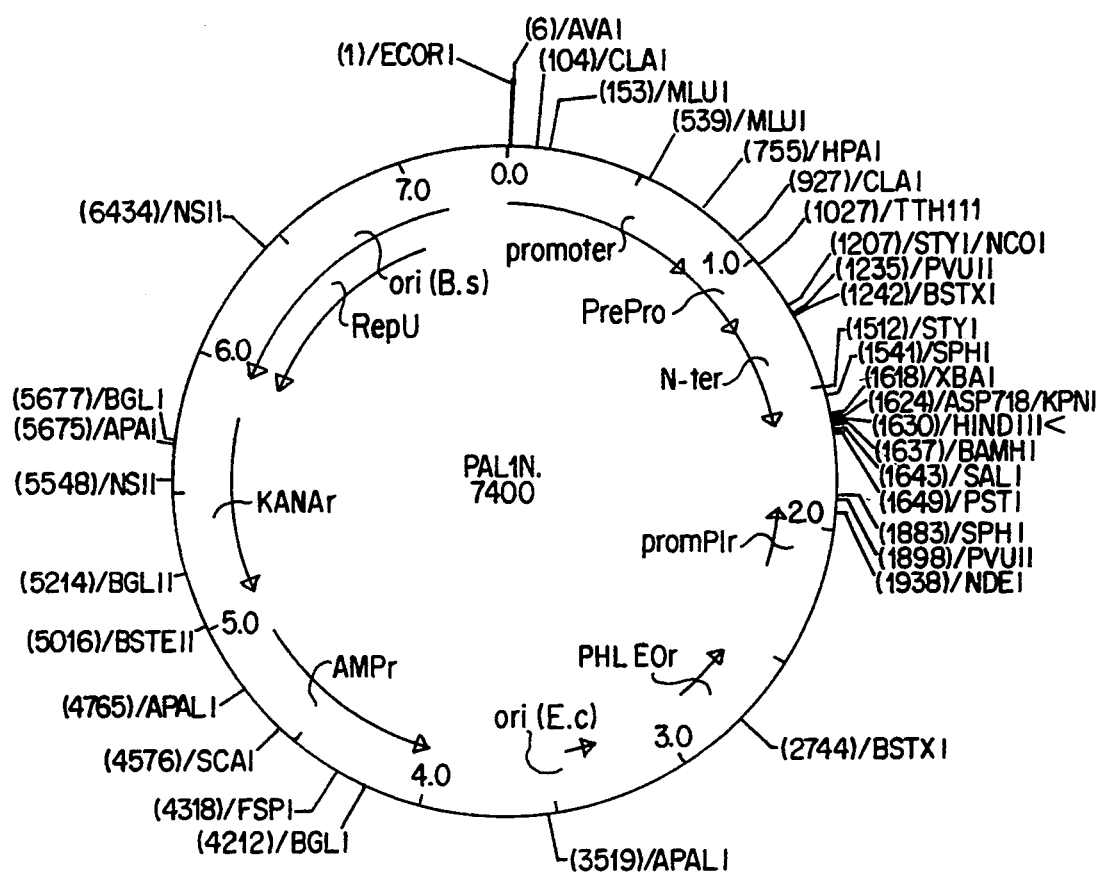
FIG. 12 shows the restriction map of the plasmid pAL1N.

The plasmid pAL1N was constructed by first cutting the vector pCLEAN4, which was obtained in Example 1, with the restriction endonucleases NcoI and XbaI, and subsequently cloning the resulting NcoI/XbaI fragment which is 414 base-pairs in size into the NcoI/XbaI site of the vector pAL1P (prepared as in Example 13). The vector pAL1N was constructed in *E. coli* MC1061, and the vector was isolated from ampicillin-resistant *E. coli* transformants. The prepared vector contains the N-terminal part of the DNA sequence which codes for the mature enzyme, and the regulatory elements for the transcription and translation of the highly alkaline protease, as well as the signal sequence and the processing sequence. The restriction map of this vector is depicted in FIG. 12.

EXAMPLE 15

Construction of the plasmid pAL1C

Figure 13:
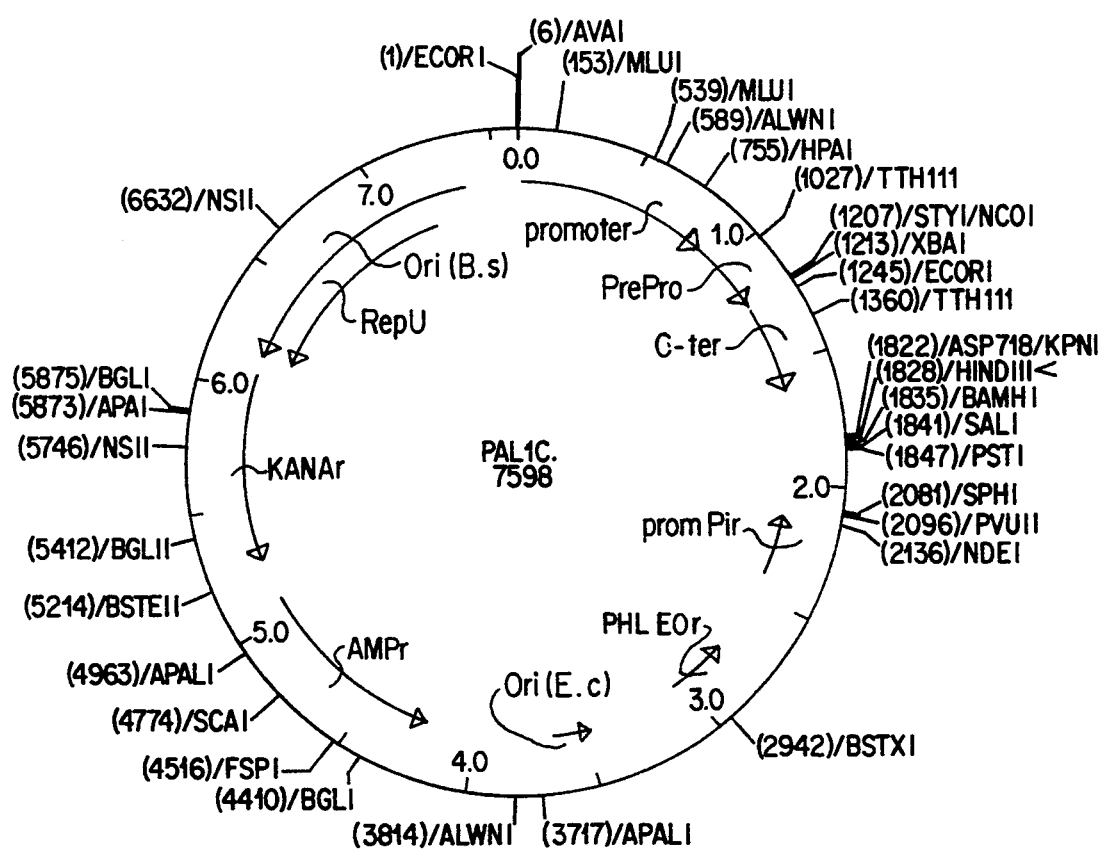
FIG. 13 shows the restriction map of the plasmid pAL1C.

The plasmid pAL1C was constructed by first cutting the vector pCLEAN4, which was obtained in Example 3, with the restriction endonucleases XbaI and Asp718, and cloning the resulting XbaI/Asp718 fragment which is 606 base-pairs in size into the XbaI/Asp718 site of the vector pAL1P (prepared in Example 13). The vector pAL1C was constructed in *E. coli* MC1061, and the vector was isolated from ampicillin-resistant *E. coli* transformants. The prepared vector contains the C-terminal part of the DNA sequence which codes for the mature protease, and the regulatory elements for the transcription and translation of the highly alkaline protease, as well as the signal sequence and the processing sequence. The restriction map of this vector is depicted in FIG. 13.

EXAMPLE 16

Construction of the expression vectors pAL1NC

Expression vectors with mutations in the C-terminal part of the protease DNA sequence, expression vectors with mutations in the N-terminal part of the protease DNA sequence, expression vectors with mutations in the N- and C-terminal parts of the DNA sequence and, for purposes of comparison, also expression vectors without mutations in the protease DNA sequence, were prepared.

A. Expression vectors with mutations in the N-terminal part of the DNA sequence of the protease. The mutated vector pCLMUTN1 obtained by directed mutagenesis as in Example 5 was cut with the restriction endonucleases NcoI and XbaI. The isolated NcoI/XbaI fragment which is 414 base-pairs in size (mutated N-terminal part of the protease structural gene with the mutations N18K, K27R, N42R, Q57R, A96R, Q107R, N114R, N115R, Q135R, N138R) was cloned into the NcoI/XbaI site of the plasmid pAL1C obtained as in Example 15. The resulting vector represents a complete expression vector with suitable reading frame for the expression of the mutated protease. The vectors were given the following names:

pALN18K = expression vector for the protease with the N18K mutation;
pALK27R = expression vector for the protease with the K27R mutation;
pALN42R = expression vector for the protease with the N42R mutation;
pALQ57R = expression vector for the protease with the 057R mutation;
pALA96R = expression vector for the protease with the A96R mutation;
pALQ107R = expression vector for the protease with the Q107R mutation;
pALN114R = expression vector for the protease with the N114R mutation;
pALN115R = expression vector for the protease with the N115R mutation;
pALQ135R = expression vector for the protease with the Q135R mutation;
pALN138R = expression vector for the protease with the N138R mutation;
pAL27/115 = expression vector for the protease with the K27R/N115R mutation;
pAL27/135 = expression vector for the protease with the K27R/Q135R mutation.

B. Expression vectors with mutations in the C-terminal part of the DNA sequence of the protease.

The mutated vector pCLMUTC1 obtained by directed mutagenesis as in Example 5 was cut with the restriction endonucleases XbaI and Asp718. The isolated XbaI/Asp718 fragment which is 606 base-pairs in size (mutated C-terminal part of the protease structural gene with the mutations A166R, V238R, N255R, S259K, A266R) was cloned into the XbaI/Asp718 site of the plasmid pAL1N obtained as in Example 14. The resulting vector represents a complete expression vector with suitable reading frame for the expression of the mutated protease. The vectors were given the following names:

pALA166R = expression vector for the protease with the A166R mutation;
pALV238R = expression vector for the protease with the V238R mutation;
pALN255R = expression vector for the protease with the N255R mutation;
pALS259K = expression vector for the protease with the S259K mutation;
pALA266R = expression vector for the protease with the A266R mutation.

C. Expression vector with mutations in the C-terminal and N-terminal parts of the protease DNA sequence.

The expression vector pALA96R prepared as described above under A. and the expression vector pALA266R prepared as described above under B. in this example were each cut with the restriction endonucleases XbaI and AvaI. The fragment of the plasmid pALA96R which is 1612 base-pairs in size was ligated with the fragment of the plasmid pALA266R which is 6388 base-pairs in size. The resulting plasmid was called pAL96/266.

The plasmid called pAL107/238 was prepared in an analogous manner from the expression vector pALQ107R prepared as described above under A. and the expression vector pALV238R prepared as described above under B. in this example.

D. Expression vector with the non-mutated DNA sequence of the initial protease.

The expression vector with the non-mutated initial structural gene of the protease was obtained by either cloning the non-mutated NcoI/XbaI fragment which is 414 base-pairs in size from the plasmid pCLEAN4 obtained as in Example 3 into the NcoI/XbaI site of the plasmid pAL1C obtained as in Example 15; or by cloning the XbaI/Asp718 fragment which is 606 base-pairs in size from the plasmid pCLEAN4 obtained as in Example 3 into the XbaI/Asp718 site of the plasmid pAL1N obtained as in Example 14. The resulting vectors are complete expression vectors with suitable reading frames for expressing the non-mutated highly alkaline initial protease.

The four aforementioned expression vectors were each constructed in *E. coli*MC1061. The expression vectors were isolated from ampicillin-resistant *E. coli* transformants. The expression vectors prepared and isolated in this example were introduced into *B. subtilis* BD224 for the expression of mutated and non-mutated protease genes. In this case selection was for neomycin or phleomycin resistance. The transformants were able to produce the mutated (transformants with vectors from A., B. and C.) or the non-mutated (transformants with vector from D.) highly alkaline protease.

Figure 14:
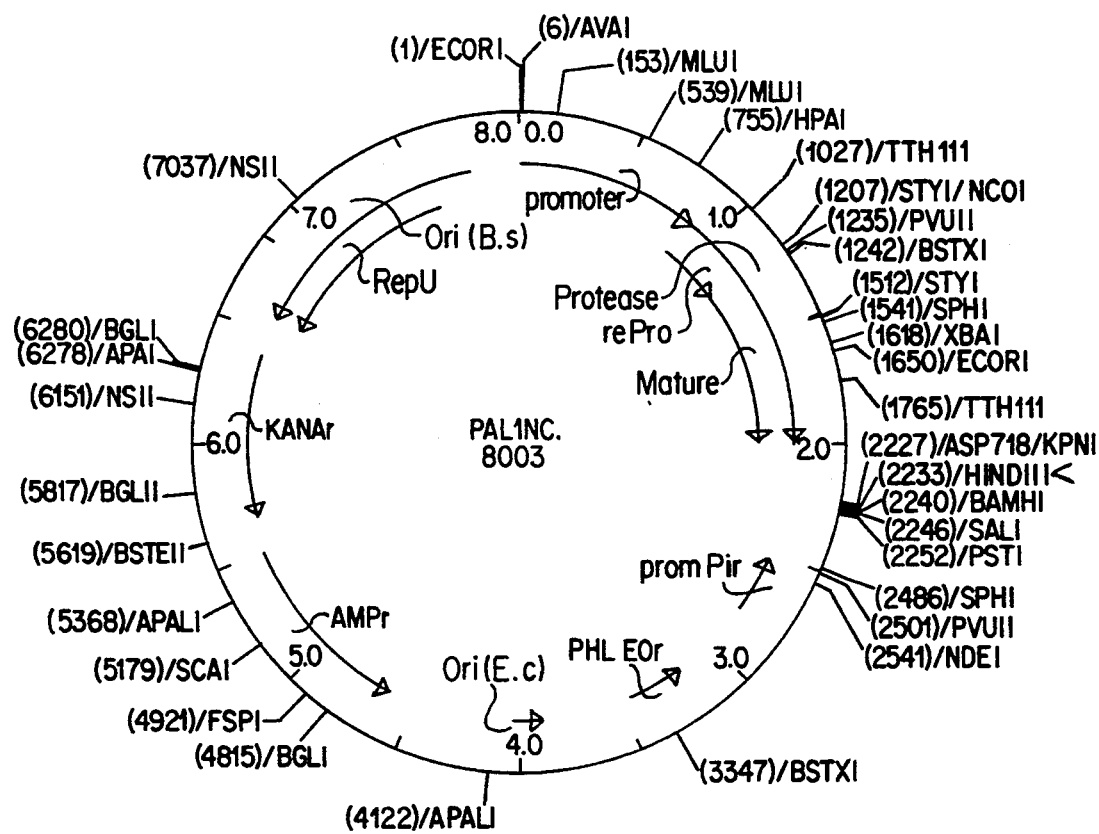
FIG. 14 shows the restriction map of the pAL1NC type expression vectors for expressing mutated and un-mutated highly alkaline proteases.

The restriction map of these vectors of the pAL1NC type is depicted in FIG. 14.

EXAMPLE 17

Synthesis of a DNA double-stranded linker

In order to synthesize a double-stranded linker which has protruding 5' ends and which is distinguished by a DNA sequence which codes for the recognition sites, which are in close proximity or follow directly one after the other in the indicated sequence, for the restriction endonucleases NcoI at the beginning, followed by XbaI and Asp718 in the middle of and HindIII at the end of the sequence, the two single-stranded DNA sequences first were each prepared separately and purified in a manner analogous to the synthesis of synthetic oligonucleotides in Example 8. The resulting DNA single strands were subsequently hybridized together to give the double strand. The prepared synthetic DNA double-stranded linker with the following sequence and following single recognition sites for restriction endonucleases 5' - CCATGGTCTAGAGGTACCA - 3' (SEQ. ID. NO. 18)
3' - CAGATCTCCATGGTTCGAA - 5' (SEQ. ID. NO. 19)
　　 ^　　　　^　　　　　^　　　　　　　^
　NcoI　　XbaI　　Asp718
　　　　　　　　　　　　　HindIII was employed for constructing the vector in Example 13.

EXAMPLE 18

Preparation of the mutated highly alkaline proteases and, for purposes of comparison, also the initial protease 50 ml of preculture medium (20 g of tryptone, 10 g of yeast extract, 5 g of NaCl, 75 g of soluble starch, 10 ml of corn steep liquor per liter) were inoculated with one colony of the strains to be tested (in each case B. subtilis BD224 transformed with one of the vectors pAL1NC prepared in Example 16). The culture was incubated at 37° C. and 250 rpm for 16 hours. 2.5 ml of this culture were used to inoculate 50 ml of main culture medium (30 g of soya meal, 90 g of potato starch, 10 g of Na caseinate and 10 ml of corn steep liquor per liter). The main culture was incubated under the same conditions as the preculture. The cultures were centrifuged after 72 hours.

The highly alkaline protease was purified from the supernatants by HPLC (Ultropac type TSK-CM-2SW column from LKB; elution buffer 0.05M sodium acetate with a pH of 6 and 0.8M sodium acetate with a pH of 6).

The washing properties of the optimized (mutated) proteases were subsequently determined by comparison with the initial (non-mutated) protease.

EXAMPLE 19

Washing tests

The washing tests were carried out in a Linitest with EMPA 117 (11 cm×11 cm; polyester/cotton blended fabric, soiled with milk, blood and permanent ink) as the test fabric (purchased from the Eidgenoessische Material pruefungsanstalt, Sankt Gallen, Switzerland)-Washing was carried out with 6 g/l IEC test detergent with perborate, type 1 (Lever Sunlicht GmbH, Mannheim; composition: 6.4% by weight linear alkylsulfonates, 2.3% by weight ethoxylated fatty alcohols with 14% ethoxy groups, 2.8% by weight sodium soap, 35% by weight sodium tripolyphosphate, 6% by weight sodium silicate, 1.5% by weight magnesium silicate, 1% by weight carboxy/methylcellulose, 0.2% by weight ethylenediaminetetraacetic acid (EDTA), 0.2% by weight optical brightener (stilbene type), 16.8% by weight sodium sulfate, and 7.8% by weight water as a spray-dried powder without bleach activator plus 20% by weight sodium perborate tetrahydrate) in water having a hardness of 15° on the German hardness scale. The pH of the wash liquor was pH 10.5. The washing time was 30 minutes at 45° C., and in each case 20 U of protease (prepared as described in Example 18) were employed per 100 ml. After the washing process was complete, the pieces of fabric were rinsed three times with tap water, dried and subsequently ironed. The reflection of the pieces of test cloth was determined four times on each side. Table 2 shows the averages of 16 washing tests in each case.

TABLE 2

| Protease | Reflection | Relative Reflection |
|---|---|---|
| Blank (without protease) | 48.8% | — |
| Initial protease | 71.1% | 100% |
| K27R | 72.8% | 107.6% |
| N42R | 71.9% | 103.6% |
| Q57R | 72.3% | 105.4% |
| Q107R | 71.6% | 102.2% |
| N115R | 71.7% | 102.7% |
| S259K | 73.6% | 111.2% |
| K27R/N115R | 74.1% | 113.5% |
| Q107R/V238R | 73% | 108.5% |

EXAMPLE 20

Washing tests

The washing tests were carried out in a manner analogous to Example 19. The washing powder used was a detergent in a formulation suitable for Europe containing an anionic and non-ionic surfactant, sodium tripolyphosphate as complexing agent, sodium silicate, sodium perborate as bleaching agent and sodium sulfate as a standardizing agent. The result of washing is shown in Table 3.

TABLE 3

| Protease | Reflection | Relative Reflection |
|---|---|---|
| Blank (without protease) | 47.4% | — |
| Initial protease | 65.6% | 100% |
| N18K | 66.2% | 103.3% |
| K27R | 66.4% | 104.4% |
| N114R | 66.5% | 104.9% |
| Q135R | 66.3% | 103.8% |
| N138R | 67.3% | 109.3% |
| A166R | 65.9% | 101.6% |
| V238R | 66% | 102.2% |
| N255R | 65.9% | 101.6% |
| K27R/Q135R | 67.4% | 109.9% |
| A96R/A266R | 66.6% | 105.5% |

The foregoing description and examples have been set forth merely to illustrate the invention and are not intended to be limiting. Since modifications of the described embodiments incorporating the spirit and substance of the invention may occur to persons skilled in the art, the invention should be construed to include all variations embraced within the scope of the appended claims and equivalents thereof.

---

What is claimed is:

1. Highly alkaline protease, which has an amino-acid sequence having at least 80% sequence similarity with the protease amino-acid sequence illustrated in FIG. 1 (SEQ. ID. NO. 2) commencing at residue number 1 at the 'protease' mark and differing from said FIG. 1 (SEQ. ID. NO. 2) sequence in from one to three of the positions 18, 42, 49, 57, 96, 107, 114, 115, 135, 138, 166, 176, 179, 188, 189, 198, 238, 255, or 266 in FIG. 1 (SEQ. ID. NO. 2), or sequence positions corresponding thereto, in that the amino acid located in the differing position has been replaced by a more strongly basic amino acid selected from the group consisting of lysine and arginine.

2. Highly alkaline protease according to claim 1, in which an amino acid in 1 or 2 of the positions indicated in claim 1, has been replaced by a more strongly basic amino acid.

3. Highly alkaline protease according to claim 1, which has a pH optimum from 10 to 12.5 and a molecular weight of 26,000 to 28,000 g/mole.

4. Highly alkaline protease according to claim 1, which has an amino-acid sequence having at least 90% sequence similarity with the amino-acid sequence illustrated in FIG. 1 (SEQ. ID. NO. 2).

5. Highly alkaline protease according to claim 4, which has an amino-acid sequence having at least 95% sequence similarity with the amino-acid sequence illustrated in FIG. 1 (SEQ. ID. NO. 2).

6. A detergent composition comprising a highly alkaline protease according to claim 1, and at least one conventional detergent ingredient.

7. A detergent composition according to claim 6, comprising at least one conventional detergent ingredient selected from the group consisting of surfactants, builders and bleaching agents.

8. A detergent composition according to claim 7, wherein said composition further comprises at least one detergent additive selected from the group consisting of enhancers, enzyme stabilizers, anti-redeposition agents, compatibility promoters, complexing and chelating agents, foam regulators, optical brighteners, opacifying agents, corrosion inhibitors, anti-electrostatic agents, dyestuffs, bactericides, bleaching agent activators, and peracid bleaching agent precursors.

9. Highly alkaline protease, which has an amino-acid sequence having at least 80% sequence similarity with the protease amino-acid sequence illustrated in FIG. 1 (SEQ. ID. NO. 2) commencing at residue number 1 at the 'protease' mark and differing from said FIG. 1 (SEQ. ID. NO. 2) sequence in from one to three of the positions 18, 49, 57, 107, 114, 115, 135, 138, 166, 176, 179, 188, 189, 198, 238, or 255 in FIG. 1 (SEQ. ID. NO. 2), or sequence positions corresponding thereto, in that the amino acid located in the differing position has been replaced by a more strongly basic amino acid selected from the group consisting of lysine and arginine.

10. Highly alkaline protease according to claim 9, in which an amino acid in 1 or 2 of the positions indicated in claim 1, has been replaced by a more strongly basic amino acid.

11. Highly alkaline protease according to claim 9, which has a pH optimum from 10 to 12.5 and a molecular weight of 26,000 to 28,000 g/mole.

12. Highly alkaline protease according to claim 9, which has an amino-acid sequence having at least 90% sequence similarity with the amino-acid sequence illustrated in FIG. 1 (SEQ. ID. NO. 2).

13. Highly alkaline protease according to claim 12, which has an amino-acid sequence having at least 95% sequence similarity with the amino-acid sequence illustrated in FIG. 1 (SEQ. ID. NO. 2).

14. A detergent composition comprising a highly alkaline protease according to claim 9, and at least one conventional detergent ingredient.

15. A detergent composition according to claim 14, comprising at least one conventional detergent ingredient selected from the group consisting of surfactants, builders and bleaching agents.

16. A detergent composition according to claim 15 wherein said composition further comprises at least one detergent additive selected from the group consisting of enhancers, enzyme stabilizers, anti-redeposition agents, compatibility promoters, complexing and chelating agents, foam regulators, optical brighteners, opacifying agents, corrosion inhibitors, anti-electrostatic agents, dyestuffs, bactericides, bleaching agent activators, and peracid bleaching agent precursors.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2280 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus alcalophilus
        ( B ) STRAIN: HA1

( i x ) FEATURE:
        ( A ) NAME/KEY: CDS
        ( B ) LOCATION: 859..1905

( i x ) FEATURE:
        ( A ) NAME/KEY: matpeptide
        ( B ) LOCATION: 1192..1902
        ( D ) OTHER INFORMATION: /product="alkaline protease"

( i x ) FEATURE:
        ( A ) NAME/KEY: sigpeptide
        ( B ) LOCATION: 859..1189

( i x ) FEATURE:
        ( A ) NAME/KEY: miscfeature
        ( B ) LOCATION: 1231..1251
        ( D ) OTHER INFORMATION: /label=OligoI
            / note="Sequence correspons to Oligo I"

( i x ) FEATURE:
        ( A ) NAME/KEY: miscfeature
        ( B ) LOCATION: 1264..1290
        ( D ) OTHER INFORMATION: /label=OligII
            / note="Sequence corresponds to Oligo II"

( i x ) FEATURE:
        ( A ) NAME/KEY: miscfeature
        ( B ) LOCATION: 1298..1326
        ( D ) OTHER INFORMATION: /label=OligoIII
            / note="Sequence corresponds to Oligo III"

( i x ) FEATURE:
        ( A ) NAME/KEY: miscfeature
        ( B ) LOCATION: 1348..1368
        ( D ) OTHER INFORMATION: /label=OligoIV
            / note="Sequence corresponds to Oligo IV"

( i x ) FEATURE:
        ( A ) NAME/KEY: miscfeature
        ( B ) LOCATION: 1462..1488
        ( D ) OTHER INFORMATION: /label=OligoV
            / note="Sequence corresponds to Oligo V"

( i x ) FEATURE:
        ( A ) NAME/KEY: miscfeature
        ( B ) LOCATION: 1501..1521
        ( D ) OTHER INFORMATION: /label=OligoVI
            / note="Sequence corresponds to Oligo VI"

( i x ) FEATURE:
        ( A ) NAME/KEY: miscfeature
        ( B ) LOCATION: 1522..1545
        ( D ) OTHER INFORMATION: /label=OligoVII
            / note="Sequence corresponds to Oligo VII"

( i x ) FEATURE:
        ( A ) NAME/KEY: miscfeature
        ( B ) LOCATION: 1522..1548
        ( D ) OTHER INFORMATION: /label=OligoVIII
            / note="Sequence corresponds to Oligo VIII"

( i x ) FEATURE:
        ( A ) NAME/KEY: miscfeature (B) LOCATION: 1585..1611
(D) OTHER INFORMATION: /label=OligoIX
/ note="Sequence corresponds to Oligo IX"

(ix) FEATURE:
(A) NAME/KEY: miscfeature
(B) LOCATION: 1591..1617
(D) OTHER INFORMATION: /label=OligoX
/ note="Sequence corresponds to Oligo X"

(ix) FEATURE:
(A) NAME/KEY: miscfeature
(B) LOCATION: 1675..1701
(D) OTHER INFORMATION: /label=OligoXI
/ note="Sequence corresponds to Oligo XI"

(ix) FEATURE:
(A) NAME/KEY: miscfeature
(B) LOCATION: 1892..1913
(D) OTHER INFORMATION: /label=OligoXII
/ note="Sequence corresponds to Oligo XII"

(ix) FEATURE:
(A) NAME/KEY: miscfeature
(B) LOCATION: 1942..1968
(D) OTHER INFORMATION: /label=OligoXIII
/ note="Sequence corresponds to Oligo XIII"

(ix) FEATURE:
(A) NAME/KEY: miscfeature
(B) LOCATION: 1956..1982
(D) OTHER INFORMATION: /label=OligoXIV
/ note="Sequence corresponds to Oligo XIV"

(ix) FEATURE:
(A) NAME/KEY: miscfeature
(B) LOCATION: 1967..1998
(D) OTHER INFORMATION: /label=OligoXV
/ note="Sequence corresponds to Oligo XV"

(xi) SEQUENCE DESCRIPTION: SEQ ID NO:1:

```
CTCGGGAAGC CGATTTGCTA CTGCATGTCG TCGATTATTC AAATGAACGC CATCGCGAAA        60

TGGCAAAGAC GACAAATGAA ACACTCCAGG CAATGGAAAT CGATCGCCCG ATGATTTATG       120

TTTACAACAA AATGGATCAA GTGAAAGACG CGTTTCCTCA AGCGCATGGC ACGAGCTGTT       180

TATATCAGCT AAGGCTAAAC AAGGGCTTGA TTTATTAGCA CAGAAAATAG CAAGCTATGT       240

TTTTCAAGAT TTTGAAAAAC ATCTGTTCAT CATTCCTTAT CGTGACGGGG AGGCGGCTGC       300

TTATTTAAAC AACCATGCCC ATGTCCACAC ACAGCGTGCT GAGGAGGACG GCTGGCATAT       360

CGTTGCCGAT TTGCATGAAC GAGACTTAAA ACGGGTTGAA AGCTACTGTG TTTCAAAAGA       420

ACGATAATGA AAAAAGCCAT TTGAATGCTT CTTGTTCAAA TGGCTTTTTG GCGACTATGG       480

TAGACAGATG AACACTTGTT TCGCTGTTTT ACGACAAAGA TCATCTTGCC TGTTACGCGT       540

TTTTTAAATC CGTTTTCGCA CGTTCAATTG TCGCCGAGTC GTACCAGTCG CTGTAAGTGA       600

GAATATGTTT AGAAAGCCGC GTATTTAAGC GCAGTCTTTT TCGTTCTGTA CTGGCTGGTT       660

TGTGGACAGT TTCCATACCC ATCAACCTCC TTTTATTTGT AGCTTTCCCC ACTTGAAACC       720

GTTTTAATCA AAAACGAAGT GAGAAGATTC AGTTAACTTA ACGTTAATAT TTGTTTCCCA       780

ATAGGCAAAT CTTTCTAACT TTGATACGTT TAAACTACCA GCTTGGACAA GTTGGTATAA       840
```

| AAATGAGGAG GGAACCGA ATG AAG AAA CCG TTG GGG AAA ATT GTC GCA AGC | | | | | | | | | | | 891 |
|---|---|---|---|---|---|---|---|---|---|---|---|
| | Met | Lys | Lys | Pro | Leu | Gly | Lys | Ile | Val | Ala | Ser |
| | -111 | -110 | | | | -105 | | | | | |

| ACC | GCA | CTA | CTC | ATT | TCT | GTT | GCT | TTT | AGT | TCA | TCG | ATC | GCA | TCG | GCT | 939 |
|---|---|---|---|---|---|---|---|---|---|---|---|---|---|---|---|---|
| Thr | Ala | Leu | Leu | Ile | Ser | Val | Ala | Phe | Ser | Ser | Ser | Ile | Ala | Ser | Ala | |
| -100 | | | | -95 | | | | | -90 | | | | | -85 | | |

| GCT | GAA | GAA | GCA | AAA | GAA | AAA | TAT | TTA | ATT | GGC | TTT | AAT | GAG | CAG | GAA | 987 |
|---|---|---|---|---|---|---|---|---|---|---|---|---|---|---|---|---|
| Ala | Glu | Glu | Ala | Lys | Glu | Lys | Tyr | Leu | Ile | Gly | Phe | Asn | Glu | Gln | Glu | |
| | | -80 | | | | -75 | | | | | | -70 | | | | |

| | | | | | | | | | | | | | | | | |
|---|---|---|---|---|---|---|---|---|---|---|---|---|---|---|---|---|
| GCT | GTC | AGT | GAG | TTT | GTA | GAA | CAA | GTA | GAG | GCA | AAT | GAC | GAG | GTC | GCC | 1035 |
| Ala | Val | Ser | Glu -65 | Phe | Val | Glu | Gln -60 | Val | Glu | Ala | Asn | Asp | Glu -55 | Val | Ala | |
| ATT | CTC | TCT | GAG | GAA | GAG | GAA | GTC | GAA | ATT | GAA | TTG | CTT | CAT | GAA | TTT | 1083 |
| Ile | Leu | Ser -50 | Glu | Glu | Glu | Glu | Val -45 | Glu | Ile | Glu | Leu | Leu -40 | His | Glu | Phe | |
| GAA | ACG | ATT | CCT | GTT | TTA | TCC | GTT | GAG | TTA | AGC | CCA | GAA | GAT | GTG | GAC | 1131 |
| Glu | Thr -35 | Ile | Pro | Val | Leu | Ser -30 | Val | Glu | Leu | Ser | Pro -25 | Glu | Asp | Val | Asp | |
| GCG | CTT | GAA | CTC | GAT | CCA | GCG | ATT | TCT | TAT | ATT | GAA | GAG | GAT | GCA | GAA | 1179 |
| Ala | Leu -20 | Glu | Leu | Asp | Pro -15 | Ala | Ile | Ser | Tyr | Ile -10 | Glu | Glu | Asp | Ala | Glu -5 | |
| GTA | ACG | ACA | ATG | GCG | CAA | TCA | GTG | CCA | TGG | GGA | ATT | AGC | CGT | GTG | CAA | 1227 |
| Val | Thr | Thr | Met | Ala 1 | Gln | Ser | Val | Pro 5 | Trp | Gly | Ile | Ser | Arg 10 | Val | Gln | |
| GCC | CCA | GCT | GCC | CAT | AAC | CGT | GGA | TTG | ACA | GGT | TCT | GGT | GTA | AAA | GTT | 1275 |
| Ala | Pro | Ala 15 | Ala | His | Asn | Arg | Gly 20 | Leu | Thr | Gly | Ser 25 | Gly | Val | Lys | Val | |
| GCT | GTC | CTC | GAT | ACA | GGT | ATT | TCC | ACT | CAT | CCA | GAC | TTA | AAT | ATT | CGT | 1323 |
| Ala | Val | Leu 30 | Asp | Thr | Gly | Ile | Ser 35 | Thr | His | Pro | Asp 40 | Leu | Asn | Ile | Arg | |
| GGT | GGC | GCT | AGC | TTT | GTA | CCA | GGG | GAA | CCA | TCC | ACT | CAA | GAT | GGG | AAT | 1371 |
| Gly | Gly | Ala | Ser | Phe 50 | Val | Pro | Gly | Glu | Pro 55 | Ser | Thr | Gln | Asp | Gly 60 | Asn | |
| | | | | | | | | | | | | | | | | |
| Gly 45 | | | | | | | | | | | | | | | | |
| GGG | CAT | GGC | ACG | CAT | GTG | GCC | GGG | ACG | ATT | GCT | GCT | TTA | AAC | AAT | TCG | 1419 |
| Gly | His | Gly | Thr | His 65 | Val | Ala | Gly | Thr 70 | Ile | Ala | Ala | Leu | Asn 75 | Asn | Ser | |
| ATT | GGC | GTT | CTT | GGC | GTA | GCG | CCG | AGC | GCG | GAA | CTA | TAC | GCT | GTT | AAA | 1467 |
| Ile | Gly | Val | Leu 80 | Gly | Val | Ala | Pro | Ser 85 | Ala | Glu | Leu | Tyr | Ala 90 | Val | Lys | |
| GTA | TTA | GGG | GCG | AGC | GGT | TCA | GGT | TCG | GTC | AGC | TCG | ATT | GCC | CAA | GGA | 1515 |
| Val | Leu | Gly 95 | Ala | Ser | Gly | Ser | Gly 100 | Ser | Val | Ser | Ser | Ile 105 | Ala | Gln | Gly | |
| TTG | GAA | TGG | GCA | GGG | AAC | AAT | GGC | ATG | CAC | GTT | GCT | AAT | TTG | AGT | TTA | 1563 |
| Leu | Glu | Trp | Ala 110 | Gly | Asn | Asn | Gly | Met 115 | His | Val | Ala | Asn | Leu 120 | Ser | Leu | |
| GGA | AGC | CCT | TCG | CCA | AGT | GCC | ACA | CTT | GAG | CAA | GCT | GTT | AAT | AGC | GCG | 1611 |
| Gly | Ser | Pro | Ser 125 | Pro | Ser | Ala | Thr | Leu 130 | Glu | Gln | Ala | Val | Asn 135 | Ser | Ala 140 | |
| ACT | TCT | AGA | GGC | GTT | CTT | GTT | GTA | GCG | GCA | TCT | GGG | AAT | TCA | GGT | GCA | 1659 |
| Thr | Ser | Arg | Gly | Val 145 | Leu | Val | Val | Ala | Ala 150 | Ser | Gly | Asn | Ser | Gly 155 | Ala | |
| GGC | TCA | ATC | AGC | TAT | CCG | GCC | CGT | TAT | GCG | AAC | GCA | ATG | GCA | GTC | GGA | 1707 |
| Gly | Ser | Ile | Ser 160 | Tyr | Pro | Ala | Arg | Tyr 165 | Ala | Asn | Ala | Met | Ala 170 | Val | Gly | |
| GCT | ACT | GAC | CAA | AAC | AAC | AAC | CGC | GCC | AGC | TTT | TCA | CAG | TAT | GGC | GCA | 1755 |
| Ala | Thr | Asp | Gln | Asn 175 | Asn | Asn | Arg | Ala | Ser 180 | Phe | Ser | Gln | Tyr | Gly 185 | Ala | |
| GGG | CTT | GAC | ATT | GTC | GCA | CCA | GGT | GTA | AAC | GTG | CAG | AGC | ACA | TAC | CCA | 1803 |
| Gly | Leu | Asp | Ile | Val 190 | Ala | Pro | Gly | Val | Asn 195 | Val | Gln | Ser | Thr | Tyr 200 | Pro | |
| GGT | TCA | ACG | TAT | GCC | AGC | TTA | AAC | GGT | ACA | TCG | ATG | GCT | ACT | CCT | CAT | 1851 |
| Gly | Ser | Thr | Tyr 205 | Ala | Ser | Leu | Asn | Gly 210 | Thr | Ser | Met | Ala | Thr 215 | Pro | His 220 | |
| GTT | GCA | GGT | GCA | GCA | GCC | CTT | GTT | AAA | CAA | AAG | AAC | CCA | TCT | TGG | TCC | 1899 |
| Val | Ala | Gly | Ala | Ala 225 | Ala | Leu | Val | Lys | Gln 230 | Lys | Asn | Pro | Ser | Trp 235 | Ser | |
| AAT | GTA | CAAATCCGCA | ATCATCTAAA | GAATACGGCA | ACGAGCTTAG | GAAGCACGAA | | | | | | | | | | 1955 |
| Asn | Val | | | | | | | | | | | | | | | |
| CTTGTATGGA | AGCGGACTTG | TCAATGCAGA | AGCGGCAACA | CGCTAATCAA | TAAAAAAGC | | | | | | | | | | | 2015 |
| CTGTGCGGTT | AAAGGGCACA | GCGTTTTTTT | GTGTATGAAT | CGAAAAAGAG | AACAGATCGC | | | | | | | | | | | 2075 |

```
AGGTCTCAAA AATCGAGCGT AAAGGGCTGT TTAAAGCTCT TTACGCTCGC AGGTCTTATC    2135

GCTATACAAT GGAAAATTCA CGTCTTTTGA CTTTCATGGC ATATTTATTT AAGTATTCGT    2195

TTGCTTTTTC GTACTCTCCG TTTTTCTGGT ACCATTGCGC CAGCTCAATT GCATAGTGGA    2255

CTGGTTCTTC TTTATTATCA AGCTT                                          2280
```

( 2 ) INFORMATION FOR SEQ ID NO:2:

( i ) SEQUENCE CHARACTERISTICS:
        ( A ) LENGTH: 349 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Lys  Pro  Leu  Gly  Lys  Ile  Val  Ala  Ser  Thr  Ala  Leu  Leu  Ile
-111 -110                -105                -100

Ser  Val  Ala  Phe  Ser  Ser  Ser  Ile  Ala  Ser  Ala  Ala  Glu  Glu  Ala  Lys
-95                 -90                      -85                           -80

Glu  Lys  Tyr  Leu  Ile  Gly  Phe  Asn  Glu  Gln  Glu  Ala  Val  Ser  Glu  Phe
                -75                      -70                           -65

Val  Glu  Gln  Val  Glu  Ala  Asn  Asp  Glu  Val  Ala  Ile  Leu  Ser  Glu  Glu
               -60                 -55                      -50

Glu  Glu  Val  Glu  Ile  Glu  Leu  Leu  His  Glu  Phe  Glu  Thr  Ile  Pro  Val
          -45                 -40                      -35

Leu  Ser  Val  Glu  Leu  Ser  Pro  Glu  Asp  Val  Asp  Ala  Leu  Glu  Leu  Asp
     -30                 -25                      -20

Pro  Ala  Ile  Ser  Tyr  Ile  Glu  Glu  Asp  Ala  Glu  Val  Thr  Thr  Met  Ala
-15                 -10                       -5                            1

Gln  Ser  Val  Pro  Trp  Gly  Ile  Ser  Arg  Val  Gln  Ala  Pro  Ala  Ala  His
               5                    10                      15

Asn  Arg  Gly  Leu  Thr  Gly  Ser  Gly  Val  Lys  Val  Ala  Val  Leu  Asp  Thr
          20                    25                      30

Gly  Ile  Ser  Thr  His  Pro  Asp  Leu  Asn  Ile  Arg  Gly  Gly  Ala  Ser  Phe
          35                    40                      45

Val  Pro  Gly  Glu  Pro  Ser  Thr  Gln  Asp  Gly  Asn  Gly  His  Gly  Thr  His
50                  55                      60                            65

Val  Ala  Gly  Thr  Ile  Ala  Ala  Leu  Asn  Asn  Ser  Ile  Gly  Val  Leu  Gly
               70                      75                            80

Val  Ala  Pro  Ser  Ala  Glu  Leu  Tyr  Ala  Val  Lys  Val  Leu  Gly  Ala  Ser
               85                      90                      95

Gly  Ser  Gly  Ser  Val  Ser  Ser  Ile  Ala  Gln  Gly  Leu  Glu  Trp  Ala  Gly
          100                   105                     110

Asn  Asn  Gly  Met  His  Val  Ala  Asn  Leu  Ser  Leu  Gly  Ser  Pro  Ser  Pro
115                      120                     125

Ser  Ala  Thr  Leu  Glu  Gln  Ala  Val  Asn  Ser  Ala  Thr  Ser  Arg  Gly  Val
130                 135                     140                          145

Leu  Val  Val  Ala  Ala  Ser  Gly  Asn  Ser  Gly  Ala  Gly  Ser  Ile  Ser  Tyr
               150                     155                     160

Pro  Ala  Arg  Tyr  Ala  Asn  Ala  Met  Ala  Val  Gly  Ala  Thr  Asp  Gln  Asn
               165                     170                     175

Asn  Asn  Arg  Ala  Ser  Phe  Ser  Gln  Tyr  Gly  Ala  Gly  Leu  Asp  Ile  Val
          180                     185                     190

Ala  Pro  Gly  Val  Asn  Val  Gln  Ser  Thr  Tyr  Pro  Gly  Ser  Thr  Tyr  Ala
195                      200                     205

Ser  Leu  Asn  Gly  Thr  Ser  Met  Ala  Thr  Pro  His  Val  Ala  Gly  Ala  Ala
```

|210|215|220|225|
|---|---|---|---|

Ala Leu Val Lys Gln Lys Asn Pro Ser Trp Ser Asn Val
                    230                 235

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..19
        ( D ) OTHER INFORMATION: /note="Linker second strand"

( x i ) SEQUENCE DESCRIPTION: SEQ ID NO:3:

AAGCTTGGTA CCTCTAGAC                                                                 19

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..30
        ( D ) OTHER INFORMATION: /note="Oligo II: Lys27-.Arg"

( x i ) SEQUENCE DESCRIPTION: SEQ ID NO:4:

TCTGGTGTAC GTGTTGCAGT ACTCGATACA                                                     30

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..21
        ( D ) OTHER INFORMATION: /note="Oligo III: Asn42-.Arg"

( x i ) SEQUENCE DESCRIPTION: SEQ ID NO:5:

CCAGACTTAC GTATTCGTGG T                                                              21

( 2 ) INFORMATION FOR SEQ ID NO:6:

( i ) SEQUENCE CHARACTERISTICS:
        ( A ) LENGTH: 27 base pairs ( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus alcalophilus
( B ) STRAIN: HA1

( i x ) FEATURE:
( A ) NAME/KEY: miscfeature
( B ) LOCATION: 1..27
( D ) OTHER INFORMATION: /note="Oligo IV: Gln57-.Arg"

( x i ) SEQUENCE DESCRIPTION: SEQ ID NO:6:

GAACCATCCA CGCGTGATGG GAATGGG    27

( 2 ) INFORMATION FOR SEQ ID NO:7:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus alcalophilus
( B ) STRAIN: HA1

( i x ) FEATURE:
( A ) NAME/KEY: miscfeature
( B ) LOCATION: 1..27
( D ) OTHER INFORMATION: /note="Oligo V: Ala96-.Arg"

( x i ) SEQUENCE DESCRIPTION: SEQ ID NO:7:

GTTAAAGTAC TTGGGCGTAG CGGTTCA    27

( 2 ) INFORMATION FOR SEQ ID NO:8:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus alcalophilus
( B ) STRAIN: HA1

( i x ) FEATURE:
( A ) NAME/KEY: miscfeature
( B ) LOCATION: 1..21
( D ) OTHER INFORMATION: /note="Oligo VI: Gln107-.Arg"

( x i ) SEQUENCE DESCRIPTION: SEQ ID NO:8:

TCGATTGCGC GCGGATTGGA A    21

( 2 ) INFORMATION FOR SEQ ID NO:9:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus alcalophilus
( B ) STRAIN: HA1

( i x ) FEATURE:
   ( A ) NAME/KEY: miscfeature
   ( B ) LOCATION: 1..24
   ( D ) OTHER INFORMATION: /note="Oligo VII: Asn114-.Arg"

( x i ) SEQUENCE DESCRIPTION: SEQ ID NO:9:

TGGGCAGGGC GTAATGGTAT GCAC      24

( 2 ) INFORMATION FOR SEQ ID NO:10:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA (genomic)

( v i ) ORIGINAL SOURCE:
   ( A ) ORGANISM: Bacillus alcalophilus
   ( B ) STRAIN: HA1

( i x ) FEATURE:
   ( A ) NAME/KEY: miscfeature
   ( B ) LOCATION: 1..27
   ( D ) OTHER INFORMATION: /note="Oligo VIII: Asn115-.Arg"

( x i ) SEQUENCE DESCRIPTION: SEQ ID NO:10:

TGGGCAGGTA ACCGTGGCAT GCACGTT      27

( 2 ) INFORMATION FOR SEQ ID NO:11:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA (genomic)

( v i ) ORIGINAL SOURCE:
   ( A ) ORGANISM: Bacillus alcalophilus
   ( B ) STRAIN: HA1

( i x ) FEATURE:
   ( A ) NAME/KEY: miscfeature
   ( B ) LOCATION: 1..27
   ( D ) OTHER INFORMATION: /note="Oligo IX: Gln135-.Arg"

( x i ) SEQUENCE DESCRIPTION: SEQ ID NO:11:

ACACTTGAGC GTGCTGTTAA CAGCGCG      27

( 2 ) INFORMATION FOR SEQ ID NO:12:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: DNA (genomic)

( v i ) ORIGINAL SOURCE:
   ( A ) ORGANISM: Bacillus alcalophilus
   ( B ) STRAIN: HA1

( i x ) FEATURE:
   ( A ) NAME/KEY: miscfeature
   ( B ) LOCATION: 1..27
   ( D ) OTHER INFORMATION: /note="Oligo X: Gln138-.Arg"

( x i ) SEQUENCE DESCRIPTION: SEQ ID NO:12:

GAGCAAGCTG TACGTAGCGC GACTTCT      27

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..27
        ( D ) OTHER INFORMATION: /note="Oligo XI: Ala166-.Arg"

( x i ) SEQUENCE DESCRIPTION: SEQ ID NO:13:

CCGGCGCGCT ATCGTAACGC CATGGCA    27

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..22
        ( D ) OTHER INFORMATION: /note="Oligo XII: Val238-.Arg"

( x i ) SEQUENCE DESCRIPTION: SEQ ID NO:14:

CTTGGTCGAA TCGTCAAATC CG    22

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..27
        ( D ) OTHER INFORMATION: /note="Oligo XIII: Asn255-.Arg"

( x i ) SEQUENCE DESCRIPTION: SEQ ID NO:15:

TTAGGAAGCA CGCGTTTGTA TGGAAGC    27

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
    ( A ) ORGANISM: Bacillus alcalophilus
    ( B ) STRAIN: HA1

( i x ) FEATURE:
    ( A ) NAME/KEY: miscfeature
    ( B ) LOCATION: 1..27
    ( D ) OTHER INFORMATION: /note="Oligo XIV: Ser259-.Lys"

( x i ) SEQUENCE DESCRIPTION: SEQ ID NO:16:

CTTGTATGGA AAAGGCCTTG TCAATGC                    27

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus alcalophilus
        ( B ) STRAIN: HA1

( i x ) FEATURE:
        ( A ) NAME/KEY: miscfeature
        ( B ) LOCATION: 1..32
        ( D ) OTHER INFORMATION: /note="Oligo XV: Ala266-.Arg"

( x i ) SEQUENCE DESCRIPTION: SEQ ID NO:17:

GCGGACTTGT TAACGCAGAA CGTGCAACAC GC              32

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: NONE-synthetic DNA linker ( i x ) FEATURE:
        ( A ) NAME/KEY: miscfeature
        ( B ) LOCATION: 1..21
        ( D ) OTHER INFORMATION: /note="Oligo I: Asn18-.Lys"

( x i ) SEQUENCE DESCRIPTION: SEQ ID NO:18:

CCAGCAGCCC ATAAGCGTGC A                          21

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: NONE-synthetic DNA linker ( i x ) FEATURE:
        ( A ) NAME/KEY: miscfeature
        ( B ) LOCATION: 1..19
        ( D ) OTHER INFORMATION: /note="Linker first strand"

( x i ) SEQUENCE DESCRIPTION: SEQ ID NO:19:

CCATGGTCTA GAGGTACCA                            19